(12) United States Patent
Sokawa et al.

(10) Patent No.: US 7,105,154 B2
(45) Date of Patent: Sep. 12, 2006

(54) METHOD OF TREATMENT USING INTERFERON-TAU

(75) Inventors: Yoshihiro Sokawa, Kyoto (JP); Chih-Ping Liu, San Francisco, CA (US)

(73) Assignee: Pepgen Corporation, Alameda, CA (US)

(*) Notice: Subject to any disclaimer, the term of this patent is extended or adjusted under 35 U.S.C. 154(b) by 326 days.

(21) Appl. No.: 10/719,472

(22) Filed: Nov. 21, 2003

(65) Prior Publication Data

US 2004/0191217 A1 Sep. 30, 2004

Related U.S. Application Data

(63) Continuation-in-part of application No. 10/698,927, filed on Oct. 31, 2003, now abandoned, which is a continuation-in-part of application No. 10/346,269, filed on Jan. 16, 2003, which is a continuation-in-part of application No. 09/910,406, filed on Jul. 19, 2001.

(60) Provisional application No. 60/349,658, filed on Jan. 16, 2002, provisional application No. 60/219,128, filed on Jul. 19, 2000.

(51) Int. Cl.
*A61K 38/21* (2006.01)

(52) U.S. Cl. .................... 424/85.4; 436/501
(58) Field of Classification Search .............. None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,766,068 A | 8/1988 | Oeda et al. |
| 4,769,238 A | 9/1988 | Rutter |
| 5,019,382 A | 5/1991 | Cummins, Jr. |
| 5,372,808 A | 12/1994 | Blatt et al. |
| 5,438,040 A | 8/1995 | Ekwuribe |
| 5,738,845 A | 4/1998 | Imakawa |
| 5,882,640 A | 3/1999 | Cummins |
| 5,906,816 A | 5/1999 | Soos et al. |
| 5,910,304 A | 6/1999 | Cummins |
| 5,958,402 A | 9/1999 | Bazer et al. |
| 6,036,949 A | 3/2000 | Richards et al. |
| 6,060,450 A | 5/2000 | Soos et al. |
| 6,191,105 B1 | 2/2001 | Ekwuribe et al. |
| 6,346,243 B1 | 2/2002 | Brod |
| 6,372,206 B1 | 4/2002 | Soos et al. |

FOREIGN PATENT DOCUMENTS

| WO | WO 90/09806 | 9/1990 |
| WO | WO 94/10313 | 5/1994 |
| WO | WO 96/28183 | 9/1996 |
| WO | WO 96/35789 | 11/1996 |
| WO | WO 00/78266 | 12/2000 |
| WO | WO 02/06343 A2 | 1/2002 |
| WO | WO 03/061720 A1 | 7/2003 |

OTHER PUBLICATIONS

Adah, S.A., et al., *Current Medicinal Chemistry* 8:1189-1212, (2001).
Alexenko, A.P., et al., *Journal of Interferon and Cytokine Research* 17:769-779, (1997).
Amidon, G.L., et al., *Peptide and Protein Drug Delivery, Alfred Benzon Symposium* 43:146-152, (1998).
Bayley, D., et al., *J Pharm Pharmacol* 47:721-724, (1995).
Bernkop-Schnürch, A. and Gilge, B., *Drug Development and Industrial Pharmacy* 26(2):107-113, (2000).
Bocci, V., *Journal of Biological Regulators and Homeostatic Agents* 4(2):81-83, (1990).
Bocci, V., *Journal of Interferon and Cytokine Research* 19:859-861, (1999).
Bartol, F.F., et al., *Biology of Reproduction* 33:745-759 abstract only (1985).
Bazer, F.W. and Johnson, H.M., *AJRI* 26:19-22 (1991).
Brod, S.A., et al., *Neurology* 44:1144-1148, (1994).
Brod, S.A., et al., *Journal of Interferon and Cytokine Research* 15:115-122, (1995).
Brod, S.A., *Arch Neurol* 54:1300-1302, (1997).
Brod, S.A., et al., *Diabetologia* 41:1227-1232, (1998).
Brod, S.A., *Journal of Interferon and Cytokine Research* 19:841-852, (1999).
Castelli, J., et al., *Biomed & Pharmacother* 52:386-390, (1998).
Choo, Q.-L., et al., *Science* 244:359-362 (1989).
Choo, Q.-L., et al., *Proc. Natl. Acad. Sci. USA*, 88:2451-2455 (1991).
Clayette, P., et al., *Pathologie Biologiel*, 47(4):553-559 (1999).
Cotler, S.J., et al., *Journal of Viral Hepatitis* 7:211-217 (2000).
Cross, J.C., et al., *Proc. Natl. Acad. Sci. USA* 88:3817-3821 (1991).
Dianzani, F., *Journal of Interferon Research* pp. 109-118, (1992).
Dieperink, E., et al., *Am. J. Psychiatry* 157:867-876 (2000).
Ecker, D.J., et al., *Journal of Biological Chemistry* 264(13):7715-7719 (1989).
Eiamtrakarn, S., et al., *Biomaterials* 23:145-152, (2002).
Gnatek, G.G., et al., *Biology of Reproduction* 41:655-663 (1989).
Helmer, S.D., et al., *J. Reprod. Fert.*, 79:83-91 (1987).
Imakawa, K., et al., *Nature*, 330:377-379 (1987).
Imakawa, K., et al., *Molecular Endocrinology*, 3:127-139 (1989).
Jacobs, B.L., et al., *Virology* 219:339-349, (1996).

(Continued)

*Primary Examiner*—Christine J. Saoud
*Assistant Examiner*—Jegatheesan Seharaseyon
(74) *Attorney, Agent, or Firm*—Judy M. Mohr; Perkins Coie LLP

(57) ABSTRACT

A method for treating a condition responsive to interferon therapy in a human subject is described. The method includes orally administering interferon-tau to the intestinal tract in an amount effective to produce an increase in the subject's blood 2', 5'-oligoadenylate synthetase (OAS) level, relative to the OAS level in the subject in the absence of interferon-tau.

6 Claims, 17 Drawing Sheets

OTHER PUBLICATIONS

Jarpe, M.A., et al., *Protein Engineering* 7(7):863-867 (1994).
Jiménez-Sáenz, M., et al., *Journal of Gstroenterology and Hepatology* 15:567-569 (2000).
Johnson, H.M.47, et al., *Scientific American* 270(5):40-47, (1994).
Le Page, C., et al., *Rev Immunogenetics* 2:374-386, (2000).
Milstein, S.J., et al., *Journal of Controlled Release* 53:259-267, (1998).
Lawson, C.M. and Beilharz, M.W., *Journal of Interferon and Cytokine Research* 19:863-867, (1999).
Magrin, S., et al., *Hepatology* 19:273-279 (1994).
Nakajima, A. and Sokawa, Y., *Journal of Interferon and Cytokine Research* 22:397-402, (2002).
Ott, T.L., et al., *Journal of Interferon Research* 11:357-364 (1991).
Pawlotsky, J. -M., et al., *Journal of Interferon and Cytokine Research* 15:857-862 (1995).
Pontzer, C.H., et al., *Biochem Biophys Res Communications* 152(2):801-807, (1988).
Pontzer, C.H., et al., *Pro Natl Acad Sci USA* 87:5945-5949, (1990).
Reddy, S.M., et al., *Drugs of Today* 35(7):537-580, (1999).
Roberts, R.M., et al., *Endocrine Review* 13(3):432-452 (1992).
Roberts, R.M., et al., *J interferon Cytokine Res* 18:805, (1998).
Saez-Royuela, F., et al., *Hepatology* 10(4):646 (1989).
Saito, H., et al., *Journal of Viral Hepatitis* 7:64-74 (2000).
Samuel, C.E., *Hokkaido J Med Sci* 69(6):1339-1347, (1994).
Samuel, C.E., *Clinical Microbiology Reviews* 14(4):778-809, (2001).
Satoh, Y.I., et al., *J Interferon Cytokine Res* 19:887-894, (1999).
Schröder, H.C., et al., *Int J Biochem* 24(1):55-63, (1992).
Shindo, M., et al., *Hepatology* 9(5):715-719, (1989).
Short, Jr., E.C., et al., *Biology of Reproduction* 44:261-268, (1991).
Singh, B.N., *Clin Pharmacokinet* 37(3):213-255, (1999).
Sood, A. and Panchagnula, R., *Chem Rev* 101:3275-3303, (2001).
Soos, J.M., et al., *Journal of Neuroimmunology* 75:43-50, (1997).
Stoll, B.R., et al., *Journal of Controlled Release* 64:217-228, (2000).
Takayama, S., et al., *J Interferon Cytokine Res* 19:895-900, (1999).
Thorbecke, G.J., et al., *Arthritis & Rheumatism* 42(1):110-118, (1999).
Trepo, C., *Journal of Viral Hepatitis* 7:250-257 (2000).
Tyring, S.K., *Interferon: Principles and Medical Applications*, Baron, et al. (eds.), Galveston TX, 1992.
Vallet, J.L., et al., *Biology of Reproduction* 37:1307-1316 (1987).
Whaley, A.E., et al., *Journal of Biological Chemistry* 269(14):10864-10868 (1994).
Witt, P.L., et al., *J Interferon Res* 12:411-413, (1992).

METHOD OF TREATMENT USING INTERFERON-TAU

This application is a continuation-in-part of U.S. application Ser. No. 10/698,927, filed Oct. 31, 2003, which is a continuation-in-part of U.S. application Ser. No. 09/910,406, filed Jul. 19, 2001, which claims the benefit of U.S. Provisional Application No. 60/219,128, filed Jul. 19, 2000. This application is also a continuation-in-part of U.S. application Ser. No. 10/346,269, filed Jan. 16, 2003, which claims the benefit of U.S. Provisional Application No. 60/349,658, filed Jan. 16, 2002. Each of these documents is incorporated herein by reference in its entirety.

FIELD OF THE INVENTION

The present invention relates to pharmaceutical compositions containing interferon-tau and methods of uses thereof. More particularly, the invention relates to methods for treating conditions responsive to interferon-tau by orally administering interferon-tau in a dose sufficient to alter the blood level of 2', 5'-oligoadenylate synthetase.

BACKGROUND OF THE INVENTION

Interferon-tau (hereinafter "IFNτ" or "interferon-τ") was discovered originally as a pregnancy recognition hormone produced by the trophectoderm of ruminant conceptuses (Imakawa, K. et al, *Nature*, 330:377–379, (1987); Bazer, F. W. and Johnson, H. M., *Am. J. Repro. Immunol.*, 26:19–22, (1991)). The distribution of the IFNτ gene is restricted to ruminants, including cattle, sheep, and goats, (Alexenko, A. P. et al., *J. Interferon and Cytokine Res.*, 19:1335–1341, (1999)) but has been shown to have activity in cells belonging to other species including humans and mice (Pontzer, C. H. et al., *Cancer Res.*, 51:5304–5307, (1991); Alexenko, A. P. et al., *J. Interferon and Cytokine Res.*, 20:817–822, (2000)). For example, IFNτ has been demonstrated to possess antiviral, (Pontzer, C. H. et al., *Biochem. Biophys. Res. Commun.*, 152:801–807, (1988)), antiproliferative, (Pontzer, C. H., et al., 1991) and immunoregulatory activities (Assal-Meliani, A., *Am. J. Repro. Immunol.*, 33:267–275 (1995)).

While IFNτ displays many of the activities classically associated with type I IFNs, such as interferon-α and interferon-β, considerable differences exist between IFNτ and the other type I IFNs. The most prominent difference is the role of IFNτ in pregnancy in ruminant species. The other IFNs have no similar activity in pregnancy recognition. Also different is viral induction. All type I IFNs, except IFNτ, are induced readily by virus and dsRNA (Roberts, et al., *Endocrine Reviews*, 13:432 (1992)). Induced IFN-α and IFN-β expression is transient, lasting approximately a few hours. In contrast, IFNτ synthesis, once induced, is maintained over a period of days (Godkin, et al., *J. Reprod. Fert.*, 65:141 (1982)). On a per-cell basis, 300-fold more IFN-τ is produced than other type I IFNs (Cross, J. C. and Roberts, R. M., *Proc. Natl. Acad. Sci. USA* 88:3817–3821 (1991)).

Another difference lies in the amino acid sequences of IFN-τ and other type I interferons. The percent amino acid sequence similarity between the interferons $\alpha_{2b}$, $\beta_1$, $\omega_1$, $\gamma$, and $\tau$ are summarized in the table below.

|  | rHuIFNα$_{2b}$ | rHuIFNβ$_1$ | rHuIFN$_1$ω$_1$ | rHuIFN$_\gamma$ | rOvIFNτ |
|---|---|---|---|---|---|
| RhuIFNα$_{2b}$ |  | 33.1 | 60.8 | 11.6 | 48.8 |
| RhuIFNβ$_1$ | 33.1 |  | 33.1 | 12.2 | 33.8 |
| RhuIFNω$_1$ | 60.8 | 33.1 |  | 10.2 | 54.9 |
| RhuIFN$_\gamma$ | 11.6 | 12.2 | 10.2 |  | 10.2 |
| rovIFNτ | 48.8 | 33.8 | 54.9 | 10.2 |  |

Sequence comparison determined from the following references:
Taniguchi et al., Gene, 10(1):11 (1980).
Adolf et al., Biochim. Biophys. Acta, 1089(2):167 (1991).
Streuli et al., Science, 209:1343 (1980).
Imakawa et al., Nature, 330:377 (1987).

Recombinant *ovine* IFNτ (rIFNτ) is 48.8 percent homologous to IFNα$_{2b}$ and 33.8 percent homologous to IFNβ$_1$. Because of this limited homology between IFNτ and IFNα and between IFNτ and IFNβ, it cannot be predicted whether or not IFNτ would behave in the same manner as IFNα or IFNβ when administered orally. IFNτ is also reported to have a low receptor binding affinity for type I receptors on human cells (Brod, S., *J. Interferon and Cytokine Res.*, 18:841 (1999); Alexenko, A. et al., *J. Interferon and Cytokine Res.*, 17:769 (1997)). Additionally, the fact that IFNτ is a non-endogeneous human protein generates the potential for systemic neutralizing antibody formation when IFNτ is introduced into the human body (Brod, S., *J. Interferon and Cytokine Res.*, 18:841 (1999). These differences between IFNτ and the other interferons make it difficult to predict whether IFNτ when administered to a human will provide a therapeutic benefit. Teachings in the art relating to oral administration of IFNα, IFNβ, or any other non-tau interferon, fail to provide a basis for drawing any expectations for IFNτ.

One limiting factor in the use of IFNτ, as well as proteins and polypeptides in general, is related to biodistribution, as affected by protein interaction with plasma proteins and blood cells, when given parenterally. The oral route of administration is even more problematic due to proteolysis in the stomach, where the acidic conditions can destroy the molecule before reaching its intended target. For example, polypeptides and protein fragments, produced by action of gastric and pancreatic enzymes, are cleaved by exo- and endopeptidases in the intestinal brush border membrane to yield di- and tri-peptides. If proteolysis by pancreatic enzymes is avoided, polypeptides are subject to degradation by brush border peptidases. Polypeptides or proteins that might survive passage through the stomach are subject to metabolism in the intestinal mucosa where a penetration barrier prevents entry into cells. For this reason, much effort has been focused on delivering proteins to the oral-pharyngeal region in the form of a lozenge or solution held in the oral cavity for a period of time.

SUMMARY OF THE INVENTION

Accordingly, it is an object of the invention to provide a method for treating a condition in a human subject that is responsive to interferon therapy.

It is another object of the invention to provide a method for treating such a condition by oral administration of IFNτ.

In one aspect, the invention includes a method for treating a condition responsive to interferon therapy in a human subject, by orally administering IFNτ to the intestinal tract of the subject in an amount effective to produce a measurable increase in the subject's blood 2', 5'-oligoadenylate synthetase (OAS) level, relative to the OAS level in the subject in the absence of IFNτ administration. The oral administration of IFNτ to the subject's intestinal tract, in such an effective amount, is continued on a regular basis of at least several times per week, for a period of at least one month.

In one embodiment, the IFNτ is *ovine* IFNτ. In specific embodiments, the *ovine* IFNτ has a sequence identified herein as SEQ ID NO:2 or SEQ ID NO:3. More generally, the IFNτ has an amino acid sequence that is at least about 80% homologous with *ovine* IFNτ. The IFNτ can be a recombinantly produced IFNτ.

The continuing administration may be carried out on a daily basis, or several times per week, e.g., every 48 hours.

In yet another embodiment, the IFNτ is administered to a subject suffering from an autoimmune disorder, such as multiple sclerosis. In this method, IFNτ is administered during the period of patient symptoms, typically over the life of the subject.

The IFNτ, in another embodiment, is administered to a subject suffering from a viral infection, such as HCV. The method may further include detecting the presence of infection in the subject, and continuing administration of the IFNτ for a period of at several months past the time when infection is no longer detected. The subject may be treated with a second antiviral agent during the period of treatment with IFNτ.

In another embodiment, the IFNτ is administered to a subject suffering from a condition characterized by cellular proliferation, such as cancer. The subject may be treated with a second anticancer agent during the period of treatment with IFNτ.

The IFNτ dosage form is preferably one that delivers the protein predominantly to the small intestine. For example, the dosage form can be comprised of a mucoadhesive polymer that protects and/or stabilizes the protein from the intestinal environment. The mucoadhesive formulation enhances binding of the interferon to cells lining the intestinal wall.

The method can further include monitoring the blood OAS level to ascertain if the OAS level is increased as a result of initial administration of IFNτ. In another embodiment, the amount of IFNτ initially administered to the patient is adjusted to achieve a measurable increase in blood OAS, relative to the level observed prior to administering oral IFNτ.

These and other objects and features of the invention will be more fully appreciated when the following detailed description of the invention is read in conjunction with the accompanying drawings.

BRIEF DESCRIPTION OF THE DRAWINGS

FIG. 4A shows blood OAS levels, expressed as a percentage of control, taken as blood OAS in mice treated with a solution of 10% maltose without interferon, in blood samples taken at time zero and at 8 hours, 16 hours, and 24 hours post IFNτ ($10^5$ U) administration. FIG. 4B shows blood OAS levels, expressed as a percentage of control, 24 hours after delivery of IFN, at concentrations of 0, $10^2$, $10^3$, $10^4$, and $10^5$ U. Each bar represents the average ±S.E. of one experiment (three mice) of two performed, with similar results.

FIG. 5A, no food and no water; FIG. 5B, water without food; FIG. 5C, food without water; FIG. 5D, both food and water. Each bar represents the average ±S.E. of one experiment (three mice) of two performed, with similar results.

BRIEF DESCRIPTION OF THE SEQUENCES

Figure 1:
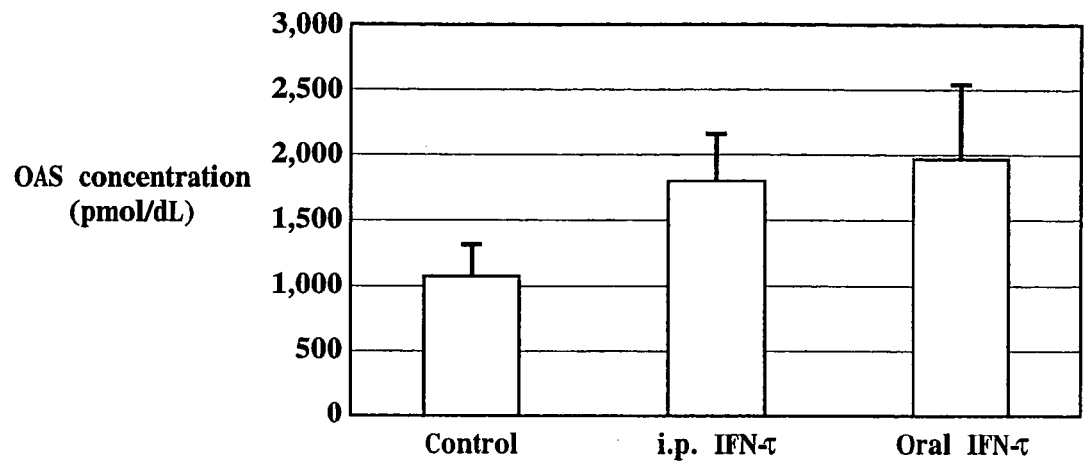
FIG. 1 shows blood OAS concentration, in pmol/dL, following intraperitoneal (i.p.) or gastric administration of IFN-τ to healthy mice.

SEQ ID NO:1 is the nucleotide sequence of a synthetic gene encoding *ovine* interferon-τ (IFNτ).

SEQ ID NO:2 corresponds to an amino acid sequence of mature *ovine* interferon-τ (IFNτ; oTP-1; GenBank Accession No. Y00287; PID g1358).

SEQ ID NO:3 corresponds to an amino acid sequence of mature *ovine* IFNτ, where the amino acid residues at positions 5 and 6 of the sequence are modified relative to the sequence of SEQ ID NO:2.

SEQ ID NO:4 is a synthetic nucleotide sequence encoding the protein of SEQ ID NO:3.

DETAILED DESCRIPTION OF THE INVENTION

I. Definitions

Interferon-tau, abbreviated as IFNτ or interferon-τ, refers to any one of a family of interferon proteins having at least one characteristic from each of the following two groups of characteristics: (i) (a) anti-luteolytic properties, (b) anti-viral properties, (c) anti-cellular proliferation properties; and (ii) about 45 to 68% amino acid homology with α-Interferons and greater than 70% amino acid homology to known IFNτ sequences (e.g., Ott, et al., *J. Interferon Res.*, 11:357 (1991); Helmer, et al., *J. Reprod. Fert.*, 79:83 (1987); Imakawa, et al., *Mol. Endocrinol,* 3:127 (1989); Whaley, et al., *J. Biol. Chem.*, 269:10846 (1994); Bazer, et al., WO 94/10313 (1994)). Amino acid homology can be determined using, for example, the LALIGN program with default parameters. This program is found in the FASTA version 1.7 suite of sequence comparison programs (Pearson and Lipman, *PNAS,* 85:2444 (1988); Pearson, *Methods in Enzymology,* 183:63 (1990); program available from William R. Pearson, Department of Biological Chemistry, Box 440, Jordan Hall, Charlottesville, Va.). IFNτ sequences have been identified in various ruminant species, including but not limited to, cow (Bovine sp., Helmer S. D., *J. Reprod. Fert.*, 79:83 (1987); Imakawa, K., *Mol. Endocrinol.,* 119:532 (1988)), sheep (*Ovine* sp.), musk ox (*Ovibos* sp.), giraffe (*Giraffa* sp., GenBank Accession no. U55050), horse (*Equus caballus*), zebra (*Equus burchelli,* GenBank Accession no. NC005027), hippopotamus (*Hippopotamus* sp.), elephant (*Loxodonta* sp.), llama (*Llama glama*), goat (*Capra* sp., GenBank Accession nos. AY357336, AY357335, AY347334, AY357333, AY357332, AY357331, AY357330, AY357329, AY357328, AY357327), and deer (Cervidae sp.). The nucleotide sequences of IFNτ for many of these species are reported in public databases and/or in the literature (see, for example, Roberts, R. M. et al., *J. Interferon and Cytokine Res.*, 18:805 (1998), Leaman D. W. et al., *J. Interferon Res.*, 12:1 (1993), Ryan, A. M. et al., *Anim. Genet.*, 34:9 (1996)). The term "interferon-tau" intends to encompass the interferon-tau protein from any ruminant species, exemplified by those recited above, that has at least one characteristic from each of the following two groups of characteristics listed above.

*Ovine* IFNτ (IFNτ) refers to a protein having the amino acid sequence as identified herein as SEQ ID NO:2, and to proteins having amino acid substitutions and alterations such as neutral amino acid substitutions that do not significantly affect the activity of the protein, such as the IFNτ protein identified herein as SEQ ID NO:3. More generally, an *ovine* IFN-τ protein is one having about 80%, more preferably 90%, sequence homology to the sequence identified as SEQ ID NO:2.

Treating a condition refers to administering a therapeutic substance effective to reduce the symptoms of the condition and/or lessen the severity of the condition.

Oral refers to any route that involves administration by the mouth or direct administration into the stomach or intestines, including gastric administration.

Intestine refers to the portion of the digestive tract that extends from the lower opening of the stomach to the anus, composed of the small intestine (duodenum, jejunum, and ileum) and the large intestine (ascending colon, transverse colon, descending colon, sigmoid colon, and rectum).

OAS level refers to the concentration or activity of blood 2', 5'-oligoadenylate synthetase (OAS) protein.

ALT refers to alanine aminotransferase.

HCV refers to hepatitis C.

"Measurable increase in blood OAS level" refers to a statistically meaningful increase in blood (serum and/or blood-cell) levels of OAS, typically at least a 25% increase over pre-treatment levels measured under identical conditions. The levels may be determined by an increase in detectable OAS enzyme or by an increase in OAS mRNA levels intracellularly, such as in blood lymphocytes. Methods for measuring OAS enzyme level in the blood are described herein using a radioiummunoassay kit, as well as in the literature (Satoh, Y. et al., *J. Interferon and Cytokine Res.*, 19:887 (1999)). Methods for measuring mRNA expression levels of OAS in cells are known in the literature (Takayama, S. et al., *J. Interferon and Cytokine Res.*, 19:895 (1999)).

II. Interferon-τ Compositions and Method of Treatment

A. Interferon-τ

The first IFNτ to be identified was *ovine* IFNτ (IFNτ), as a 18–19 kDa protein. Several isoforms were identified in conceptus (the embryo and surrounding membranes) homogenates (Martal, J., et al., *J. Reprod. Fertil.* 56:63–73 (1979)). Subsequently, a low molecular weight protein released into conceptus culture medium was purified and shown to be both heat labile and susceptible to proteases (Godkin, J. D., et al., *J. Reprod. Fertil.* 65:141–150 (1982)). IFNτ was originally called *ovine* trophoblast protein-one (oTP-1) because it was the primary secretory protein initially produced by trophectoderm of the sheep conceptus during the critical period of maternal recognition in sheep. Subsequent experiments have determined that IFNτ is a pregnancy recognition hormone essential for establishment of the physiological response to pregnancy in ruminants, such as sheep and cows (Bazer, F. W., and Johnson, H. M., *Am. J. Reprod. Immunol.* 26:19–22 (1991)).

An IFNτ cDNA obtained by probing a sheep blastocyst library with a synthetic oligonucleotide representing the N-terminal amino acid sequence (Imakawa, et al., 1987) has a predicted amino acid sequence that is 45–55% homologous with IFN-αs from human, mouse, rat, and pig and 70% homologous with bovine IFN-αII, now referred to as IFN-Ω. Several cDNA sequences have been reported which may represent different isoforms (Stewart, H. J., et al, *Mol. Endocrinol.* 2:65 (1989); Klemann, S. W., et al., *Nuc. Acids Res.* 18:6724 (1990); and Charlier, M., et al., *Mol. Cell Endocrinol.* 76:161–171 (1991)). All are approximately 1 kb with a 585 base open reading frame that codes for a 23 amino acid leader sequence and a 172 amino acid mature protein. The predicted structure of IFN-τ as a four helical bundle with the amino and carboxyl-termini in apposition further supports its classification as a type I IFN (Jarpe, M. A., et al., *Protein Engineering* 7:863–867 (1994)).

| Overview of the Interferons | | | | |
|---|---|---|---|---|
| Aspects | Type I | Type I | Type I | Type II |
| Types | α & ω | β | τ | γ |
| Produced by: | leukocyte | fibroblast | trophoblast | lymphocyte |
| Antiviral | + | + | + | + |
| Antiproliferative | + | + | + | + |
| Pregnancy Signaling | – | – | + | – |

While IFN-τ displays some of the activities classically associated with type I IFNs (see Table, above), considerable differences exist between it and the other type I IFNs. The most prominent difference is its role in pregnancy, detailed above. Also different is viral induction. All type I IFNs, except IFNτ, are induced readily by virus and dsRNA (Roberts, R. M., et al., *Endocrin. Rev.* 13:432–452 (1992)). Induced IFN-α and IFN-β expression is transient, lasting approximately a few hours. In contrast, IFN-τ synthesis, once induced, is maintained over a period of days (Godkin, et al., 1982). On a per-cell basis, 300-fold more IFN-τ is produced than other type I IFNs (Cross, J. C., and Roberts, R. M., *Proc. Natl. Acad. Sci. USA* 88:3817–3821 (1991)).

Other differences may exist in the regulatory regions of the IFNτ gene. For example, transfection of the human trophoblast cell line JAR with the gene for bovine IFNτ resulted in antiviral activity while transfection with the bovine IFN-Ω gene did not. This implies unique transacting factors involved in IFNτ gene expression. Consistent with this is the observation that while the proximal promoter region (from 126 to the transcriptional start site) of IFNτ is highly homologous to that of IFN-α and IFN-β; the region from –126 to –450 is not homologous and enhances only IFNτ expression (Cross, J. C., and Roberts, R. M., *Proc. Natl. Acad. Sci. USA* 88:3817–3821 (1991)). Thus, different regulatory factors appear to be involved in IFNτ expression as compared with the other type I IFNs.

The 172 amino acid sequence of *ovine*-IFNτ is set forth, for example, in U.S. Pat. No. 5,958,402, and its homologous bovine-IFNτ sequence is described, for example, in Helmer et al., *J. Reprod. Fert.*, 79:83–91 (1987) and Imakawa, K. et al., *Mol. Endocrinol.*, 3:127 (1989). The sequences of *ovine*-IFNτ and bovine-IFNτ from these references are hereby incorporated by reference. The amino acid sequence of *ovine* IFNτ is shown herein as SEQ ID NO:2.

1. Isolation of IFN-τ

IFNτ may be isolated from conceptuses collected from pregnant sheep and cultured in vitro in a modified minimum essential medium as described by Godkin, J. D., et al., *J. Reprod. Fertil.* 65:141–150 (1982) and Vallet, J. L., et al., *Biol. Reprod.* 37:1307 (1987). The IFNτ may be purified from the conceptus cultures by ion exchange chromotography and gel filtration. The homogeneity of isolated IFNτ may be assessed by sodium dodecyl sulfate polyacrylamide gel electrophoresis (Maniatis, T., et al., in *MOLECULAR CLONING: A LABORATORY MANUAL,* Cold Spring Harbor Laboratory, Cold Spring Harbor, N.Y. (1982); Ausubel, F. M., et al., in *CURRENT PROTOCOLS IN MOLECULAR BIOLOGY,* John Wiley & Sons, Inc., Media, Pa. (1988)), and determination of protein concentration in purified IFNτ samples may be performed using the bicinchoninic (BCA) assay (Pierce Chemical Co., Rockford, Ill.; Smith, P. K., et al., *Anal. Biochem.* 150:76 (1985)).

2. Recombinant Production of IFNτ

Recombinant IFNτ protein may be produced from any selected IFNτ polynucleotide fragment using a suitable expression system, such as bacterial or yeast cells. The isolation of IFNτ nucleotide and polypeptide sequences is described in PCT publication WO/94110313, which is incorporated by reference herein.

To make an IFNτ expression vector, an IFNτ coding sequence (e.g., SEQ ID NOS:1 or 4) is placed in an expression vector, e.g., a bacterial expression vector, and expressed according to standard methods. Examples of suitable vectors include lambda gt11 (Promega, Madison Wis.); pGEX (Smith, P. K. et al., *Anal. Biochem.* 150:76 (1985)); pGEMEX (Promega); and pBS (Strategene, La Jolla Calif.) vectors. Other bacterial expression vectors containing suitable promoters, such as the T7 RNA polymerase promoter or the tac promoter, may also be used. Cloning of the IFNτ synthetic polynucleotide into a modified pIN III omp-A expression vector is described in the Materials and Methods.

For the studies described herein, the IFNτ coding sequence present in SEQ ID NO:4 was cloned into a vector, suitable for transformation of yeast cells, containing the methanol-regulated alcohol oxidase (AOX) promoter and a Pho1 signal sequence. The vector was used to transform *P. pastoris* host cells and transformed cells were used to express the protein according to the manufacturer's instructions (Invitrogen, San Diego, Calif.).

Other yeast vectors suitable for expressing IFNτ for use with methods of the present invention include 2 micron plasmid vectors (Ludwig, D. L. et al., *Gene,* 132:33 (1993)), yeast integrating plasmids (Shaw, K. J. et al., *DNA,* 7:117 (1988)), YEP vectors (Shen, L. P. et al., *Sci. Sin.,* 29:856 (1986)), yeast centromere plasmids (YCps), and other vectors with regulatable expression (Hitzeman, R. A. et al., U.S. Pat. No. 4,775,622, issued Oct. 4, 1988; Rutter, W. J. et al., U.S. Pat. No. 4,769, 238, issued Sep. 6, 1988; Oeda, K. et al., U.S. Pat. No. 4,766,068, issued Aug. 23, 1988). Preferably, the vectors include an expression cassette containing an effective yeast promoter, such as the MFα1 promoter (Bayne, M. L. et al., *Gene* 66:235–244 (1988), GADPH promoter (glyceraldehyde-3-phosphate-dehydrogenase; Wu, D. A. et al., *DNA,* 10:201 (1991)) or the galactose-inducible GAL10 promoter (Ludwig, D. L. et al., *Gene,* 132:33 (1993); Feher, Z. et al., *Curr. Genet.,* 16:461 (1989)); Shen, L. P. et al., *Sci. Sin.,* 29:856 (1986)). The yeast transformation host is typically *Saccharomyces cerevisiae,* however, as illustrated above, other yeast suitable for transformation can be used as well (e.g., *Schizosaccharomyces pombe, Pichia pastoris* and the like).

Further, a DNA encoding an IFNτ polypeptide can be cloned into any number of commercially available vectors to generate expression of the polypeptide in the appropriate host system. These systems include the above described bacterial and yeast expression systems as well as the following: baculrus expression (Reilly, P. R. et al., BACULOVIRUS EXPRESSION VECTORS: A LABORATORY MANUAL, (1992); Beames et al., *Biotechniques*, 11:378 (1991); Clontech, Palo Alto Calif.); plant cell expression, transgenic plant expression, and expression in mammalian cells (Clontech, Palo Alto Calif.; Gibco-BRL, Gaithersburg Md.). The recombinant polypeptides can be expressed as fusion proteins or as native proteins. A number of features can be engineered into the expression vectors, such as leader sequences which promote the secretion of the expressed sequences into culture medium. The recombinantly produced polypeptides are typically isolated from lysed cells or culture media. Purification can be carried out by methods known in the art including salt fractionation, ion exchange chromatography, and affinity chromatography. Immunoaffinity chromatography can be employed, as described above, using antibodies generated based on the IFNτ, polypeptides.

In addition to recombinant methods, IFNτ proteins or polypeptides can be isolated from selected cells by affinity-based methods, such as by using appropriate antibodies. Further, IFNτ peptides (e.g. SEQ ID NOS:2 or 3) may be chemically synthesized using methods known to those skilled in the art.

B. Oral Administration of IFNτ

In studies performed in support of the invention, IFN-τ was administered orally to mice and to humans and the induction of 2',5'-oligoadenylate synthetase (OAS) activity, a recognized marker of IFN action (Shindo, M. et al., *Hepatology* 8:366–370, (1988)), in whole blood was monitored. It will be appreciated that alternative methods of monitoring OAS levels are suitable, and may offer advantages in terms of accuracy and sensitivity. For example, cellular mRNA expression levels of OAS can be measured using a semi-quantitative reverse-transcriptase PCT technique (Takayama, S. et al., *J. Interferon and Cytokine Res.*, 19:895 (1999)).

1. Administration of IFNτ to Mice

In studies performed in support of the present invention, IFNτ, administered orally, was tested for its ability to induce OAS. As described in Example 1, IFNτ was administered either orally or intraperitoneally (i.p.) to mice. OAS activity in whole blood 24 hours after IFNτ administration was determined, and the results are shown in FIG. 1.

FIG. 1 shows the OAS blood concentration, in pmol/dL, for the control animals treated with a saline containing 10% maltose was just over 1,000 pmol/dL. Mice treated with $5×10^8$ Units of IFNτ in a solution of saline containing 10% maltose intraperitoneally had an OAS blood level of about 1700 pmol/dL. Mice treated with the same IFNτ dosage orally had a blood OAS level of about 2000 pmol/dL.

Figure 2:
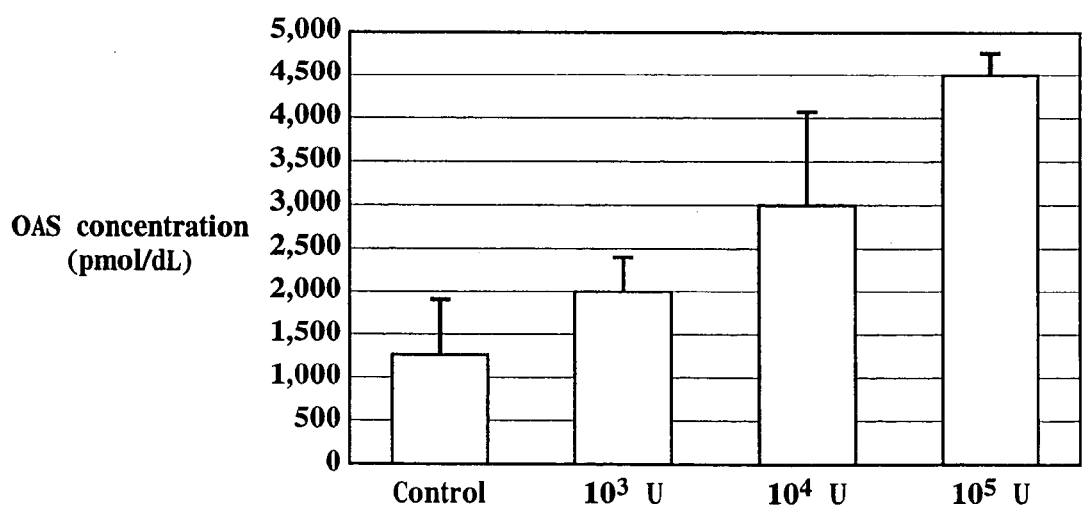
FIG. 2 shows blood OAS concentration, in pmol/dL, upon gastric administration of IFNτ to mice at dosages of $1 \times 10^3$ U, $1 \times 10^4$ U, and $1 \times 10^5$ U.

In another study, detailed in Example 2, IFNτ was administered orally in mice to determine its ability to induce OAS in a dose-dependent manner. IFNτ was orally administered in units of 0 (control), 1×103, 1×10⁴, 1×10⁵ to the upper part of the stomach in test mice. Twelve hours after oral administration, whole blood was taken from the heart and OAS concentration was determined. As shown in FIG. 2, the OAS concentration in whole blood increased in a dose dependent manner.

Example 3 describes further studies conducted on mice. In these studies before administration of IFNτ, mice were deprived of food and drink for at least six hours and IFNτ was given by orally or by intraperitoneal (i.p.) injection. When administered orally, IFNτ was introduced directly into the upper part of the stomach using an oral feeding needle.

Figure 3:
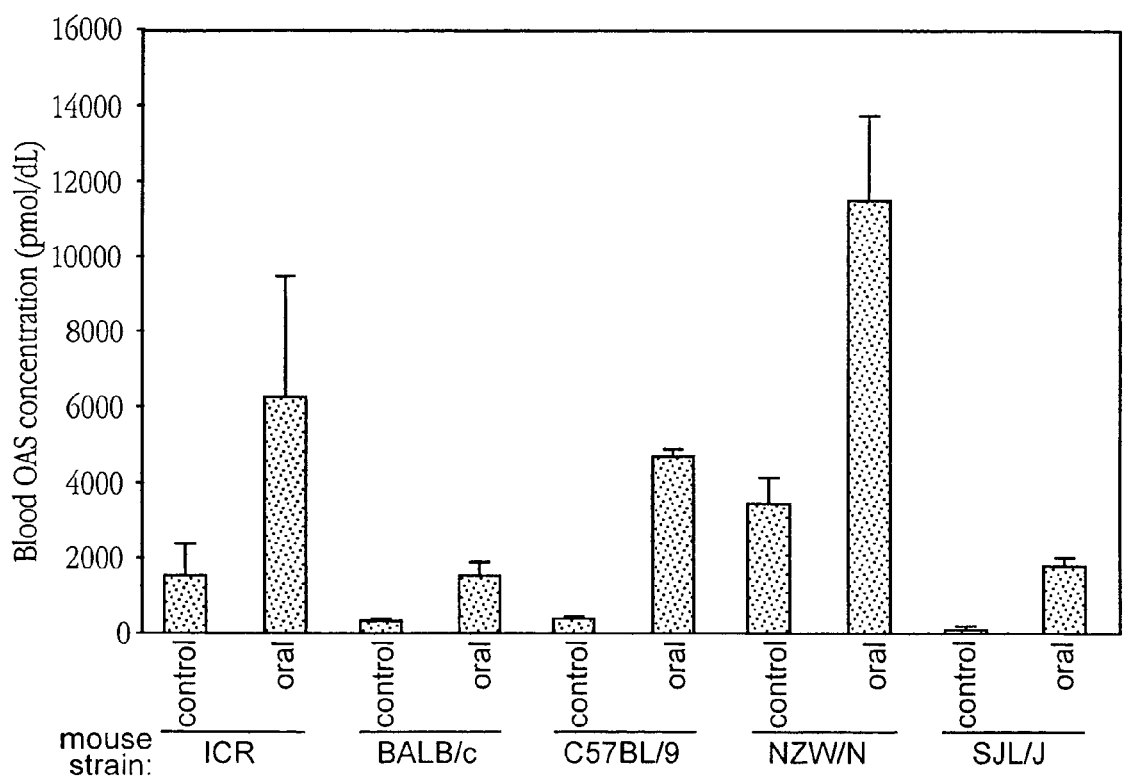
FIG. 3 is a bar graph showing blood OAS concentration, in pmol/dL, in several mouse strains (ICR, BALB/c, C57BL, NZW/N and SJL/J) following peroral administration of IFNτ ($10^5$ U). Control mice received orally a solution of 10% maltose without IFNτ. Each bar represents the average ±S.E. of one experiment (3~5 mice) of two performed, with similar results.

FIG. 3 shows the effects of gastric administration of IFNτ on the induction of OAS activity in blood in a variety of mouse strains: ICR, BALB/c, C57BL/9, NZW/N and SJL/J. All test mice were treated orally with IFNτ ($10^5$ U). Control mice received orally a solution of 10% maltose without IFNτ. Each bar represents the average ±S.E. of one experiment (3~5 mice) of two performed, with similar results. As seen in FIG. 3, the level of OAS activity in all mouse strains increased following peroral administration of IFNτ, though the extent of the increase varied with the strain. The level of activity induced in ICR, C57BL/9 and NZW/N mice was higher than that in BALB/c and SJL/J mice.

In another study, OAS activity was monitored as a function of time after administration of IFNτ. In this study, animals (ICR mice) were subjected to a six hour fast (water but no food) prior to administration of IFNτ ($10^5$ U). Blood was sampled at 8 hours, 16 hours, and 24 hours post IFN-τ administration. The results are shown in FIG. 4A.

Figure 4A:
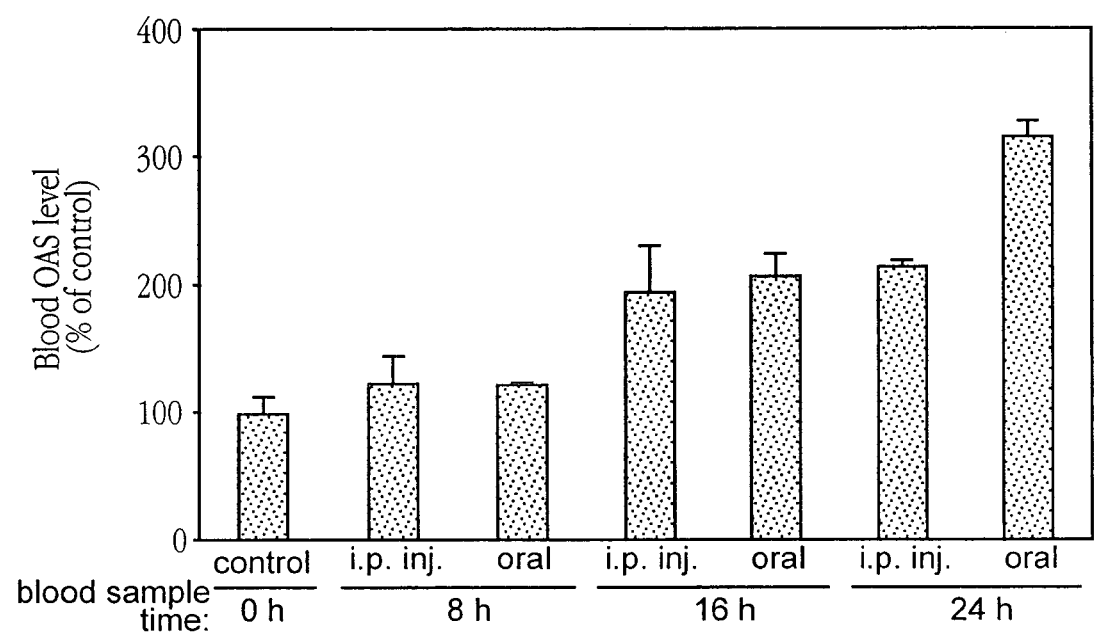
FIGS. 4A–4B are bar graphs showing induction of blood OAS activity in mice after administration of IFNτ following a 6 hour fast. IFNτ was administered orally or via intraperitoneal injection.

FIG. 4A shows blood OAS levels, expressed as a percentage of control mice, treated with the saline/10% maltose vehicle, in blood samples taken at the indicated time intervals post IFNτ administration. In FIG. 4A, each bar represents the average ±S.E. of one experiment (three mice) of two performed, with similar results. OAS activity in whole blood increased in a time-dependent manner regardless of the route, oral or i.p. injection, however, a higher level was observed at the 24 hour time point after oral administration than i.p. injection.

In another study, IFNτ at varying concentrations (0, $10^2$, $10^3$, $10^4$ and $10^5$ U), was given to mice following a six hour fast. Blood was obtained after 24 hours, and OAS activity was assayed. The results are shown in FIG. 4B.

Figure 4B:
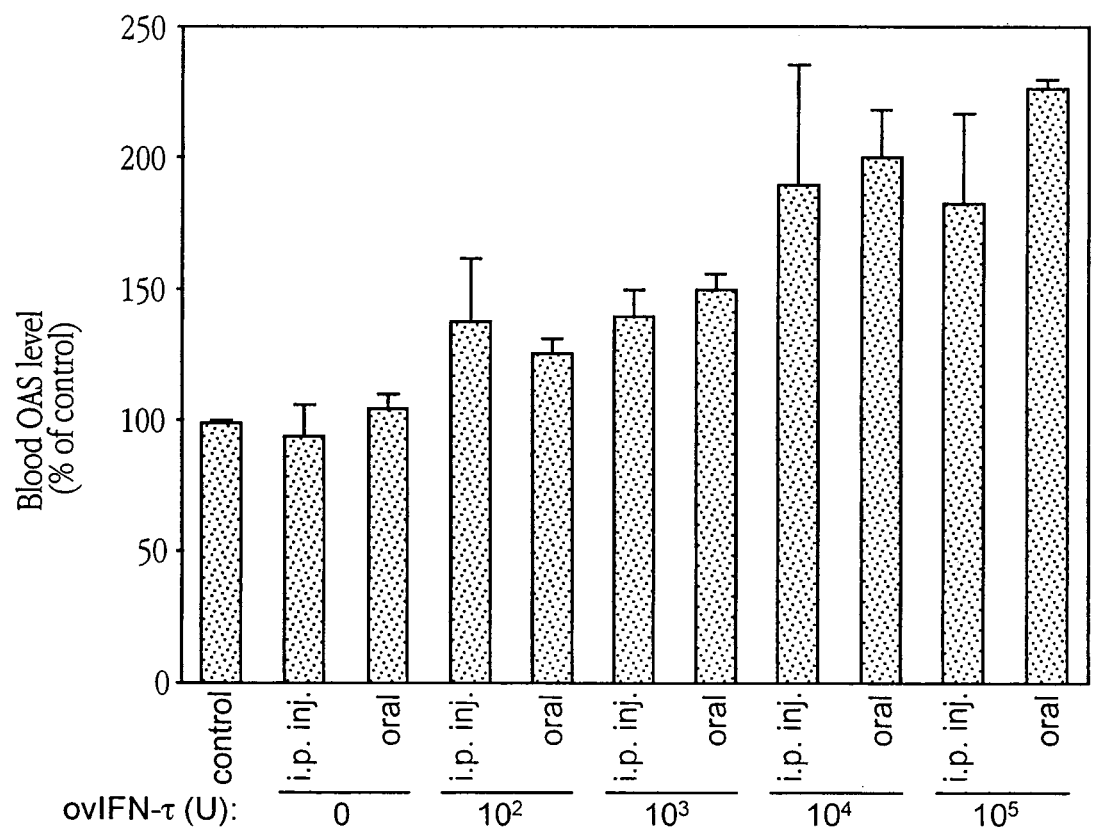
Figure 5A:
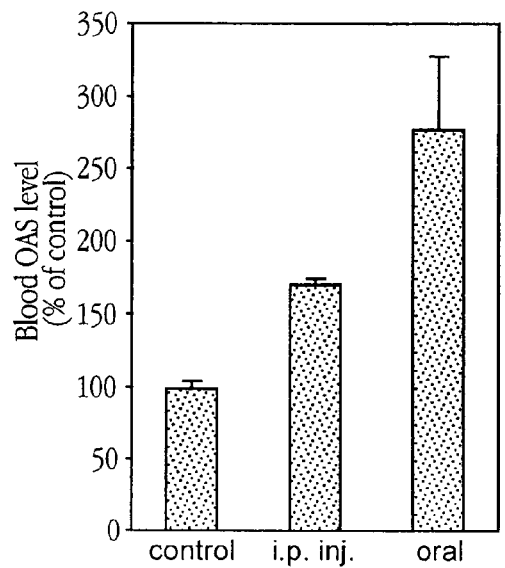
FIGS. 5A–5D are bar graphs showing the effect of fasting conditions on the induction of blood OAS in mice by administration of IFN-τ. The induction of blood OAS is shown as a percentage of control, taken as blood OAS in mice treated with a solution of 10% maltose without interferon. Treated mice received $10^4$ U of INFτ (via intraperitoneal injection or oral administration) six hours after the indicated intake regimen.
Figure 5B:
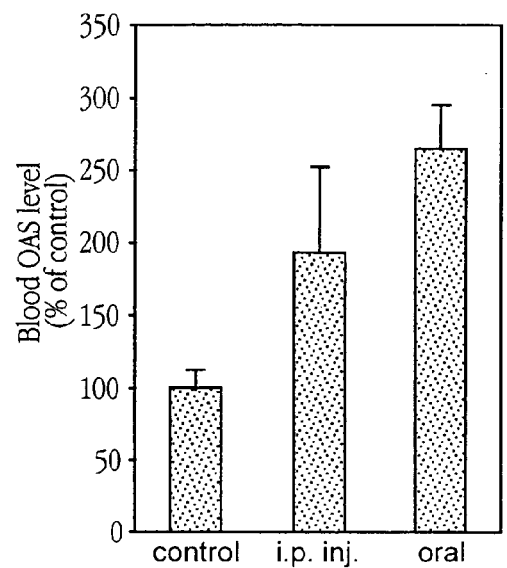
Figure 5C:
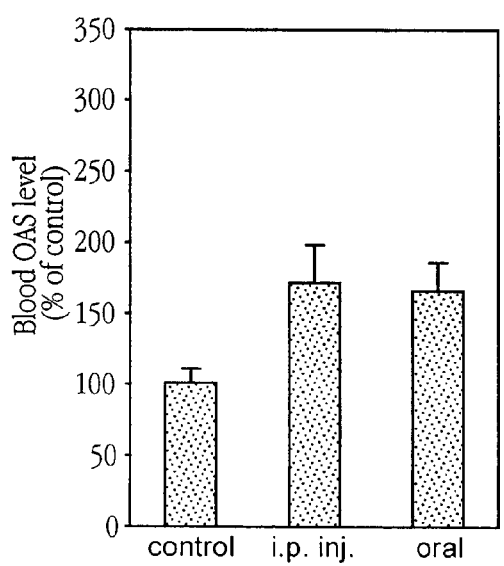
Figure 5D:
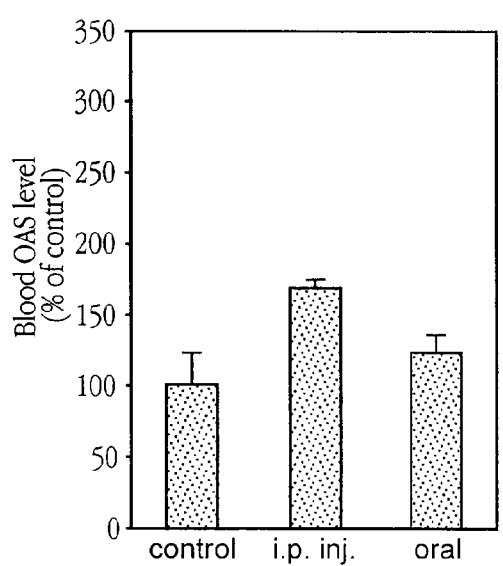

FIG. 4B shows blood OAS levels, expressed as a percentage of control mice 24 hours after delivery of IFNτ at concentrations of 0, $10^2$, $10^3$, $10^4$, and $10^5$ U. Each bar represents the average ±S.E. of one experiment (3 mice) of two performed, with similar results. Following i.p. injection, the level of activity was rather high at a low dose ($10^2$ U), and saturated at higher doses of IFN-τ ($10^4$ and $10^5$ U). In contrast, the level of activity after p.o. administration increased dose-dependently.

The data in FIGS. 4A–4B shows that IFN-τ administered orally induces a higher level of blood OAS activity than that induced by i.p. injection. In particular, the orally-induced blood OAS levels were higher than the blood OAS levels induced by i.p. injection at IFN-τ dosages of greater than about $10^3$ U and at post administration times of greater than about 8 hours.

In another study, the effect of fasting conditions on the induction of blood OAS in mice by administration of IFN-τ was evaluated. In this study, mice were subjected to a defined food and water intake regimen for six hours. After the six hour regimen, $10^4$ U of INFτ was administered by oral gavage or by intraperitoneal injection, along with food and water. The intake regimens were as follows: Case I, neither food nor water was given; Case II, water but no food was given; Case III, only food was given; Case IV, both food and water were given. Whole blood was obtained from the heart at 24 hours and levels of OAS activity were determined. The results are shown in FIGS. 5A–5D.

FIGS. 5A–5D correspond to the mice subjected to Case I–Case IV food and water intake regimens defined in the paragraph above, respectively. The results in FIGS. 5A–5D show the induction of blood OAS expressed as a percentage of control, taken as blood OAS in mice treated with a solution of 10% maltose without interferon. The results show that higher blood OAS levels are induced by oral administration of IFN-τ to subjects in a fasted state, as seen best in FIG. 5A and FIG. 5B for mice receiving no food.

In this study, it was observed that almost the same amounts of food were ingested with or without a supply of water. Water intake, however, was lower without food (case I and case II) than with food (case III and case IV). In some animals, after fasting for six hours, a 0.2 mL maltose solution containing blue dye was given orally and the distribution of the dye in the stomach and intestine was examined (data not shown). Following the ingestion of food (case III and case IV), the stomachs of mice swelled and the dye localized mainly in the stomach, probably because the food absorbed the dye. However, the dye was transferred quickly to the intestine when no food was ingested. This observation suggests that IFNτ taken orally may exert its effect in the intestine to induce high levels of OAS activity in blood.

A comparative study was done to measure the effect of oral administration of MuIFN-α on blood OAS levels. In this study, ICR mice were treated with varying concentrations (0, $10^2$, $10^3$ and $10^4$ IU) of MuIFN-α by either the p.o. or i.p. route. OAS activity in blood obtained 16 hours after MuIFN-α administration was assayed. The results are shown in FIG. 6, where each bar represents the average ±S.E. of one experiment (3 mice) of two performed, with similar results.

Figure 6:
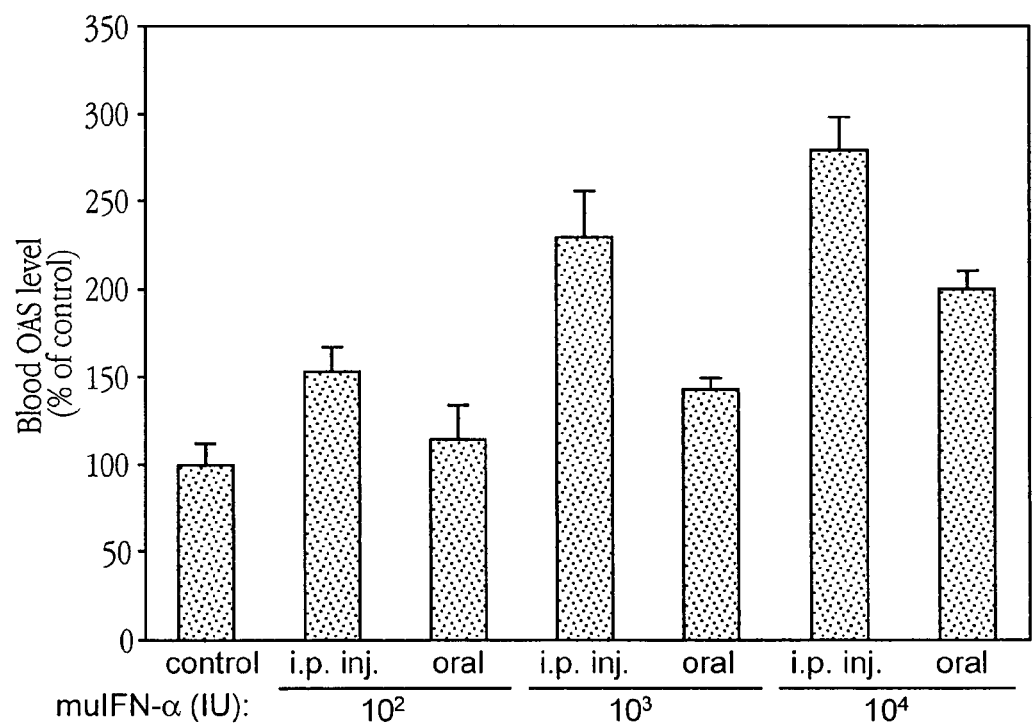
FIG. 6 is a bar graph showing induction of blood OAS activity, expressed as a percentage of control, taken as blood OAS in mice treated with a solution of 10% maltose without interferon, by administration of murine IFNα (0, $10^2$, $10^3$ and $10^4$ IU) given to ICR mice orally or via intraperitoneal injection. The OAS activity in blood was assayed 16 hours after IFNα administration. Each bar represents the average ±S.E. of one experiment (three mice) of two performed, with similar results.

FIG. 6 is a bar graph showing induction of blood OAS activity, expressed as a percentage of control mice, following administration of MuIFNα (0, $10^2$, $10^3$ and $10^4$ IU) given orally or via intraperitoneal injection. The level of OAS activity was increased dose-dependently by either route of administration, with i.p. injection resulting in better induction of blood OAS activity than p.o. administration. This result is the opposite of that observed with IFNτ, where oral administration of IFNτ, achieved a higher blood OAS level than intraperitoneal injection of IFNτ. Moreover, the body temperature of mice rose slightly when MuIFNα was administered, but not when IFNτ was used (data not shown).

The data presented in FIGS. 1–6 provide evidence that IFN administered to the intestinal tract induces or upregulates the OAS response in vivo. Although oral administration of IFNτ has been previously reported in the literature (see for example WO 96/28183), no study has shown that this non-endogenous interferon would be capable upon oral administration of inducing the OAS response. In the present studies, IFNτ was directly administered into the intestinal tract, without contact to the tunica mucosa oris, thereby ruling out any absorption in the oropharengyl region. Direct absorption of IFNτ from the stomach would diminish antibody formation against IFNτ compared to IFNτ absorbed through the oral mucosal membrane, particularly in the case of chronic administrations of IFNτ.

2. Administration to Humans Suffering from Hepatitis C

Human patients infected with hepatitis C were recruited for a study. The patients were divided into four test groups for treatment with oral IFNτ (SEQ ID NO:4). As described in Example 4, each subject in the test groups self-administered three times daily a controlled volume of a 1 mg/mL solution of IFNτ. Patients in Test Groups I, II, III, and IV received a total daily dose of 1 mg IFNτ, 3 mg IFNτ, 9 mg IFNτ, and 15 mg IFNτ, respectively. The patients returned to the test clinic at defined intervals to provide a blood sample for analysis of (i) 2',5'-oligoadenylate synthetase (OAS) levels (a) in the serum and (b) in the peripheral blood mononuclear cells; (ii) alanine aminotransferase (ALT) levels; and (iii) viral titer level (hepatitis C RNA copies per mL).

The results for some subjects in each test group are shown in Tables 3–5 below, and graphically in FIGS. 7–8. Tables 3A–3B present data for six patients in Dose Group I, treated with 0.33 mg oral IFNτ three times daily. Serum 2-5 OAS levels, in pmol/dL, are indicated in the column identified as "2-5A (Serum)". Two of the subjects, PAB/001 and JRJ/006, experienced no increase in blood OAS levels. The other four subjects had a measurable increase in blood OAS level, with subjects identified as MSM/002 and LER/004 showing a significant increase. Subject MSM/002 had a baseline OAS level of 11.0 pmol/dL. By test day 15, this had increased to 51.5, a more than four fold increase. Subject Z-I/005 had a baseline OAS level of 43.4 pmol/dL. The OAS level increased, reaching 74.8 pmol/dL by test day 29.

Table 4 presents the data for three patients in Dose Group II, treated with 1 mg IFNτ three times daily. Patients AMC/007 and DBF/012 responded to IFNτ treatment, with significantly increased blood OAS levels. For example, patient AMC/007 had a baseline OAS level of 11.2 pmol/dL. This increased steadily over the first 29 days of treatment, with a maximum of 120 pmol/dL measured on test day 29. OAS levels remained more than four-fold over the baseline level throughout test day 71. Patient DBF/012 had an initial OAS level of 28.8 pmol/dL, prior to treatment. This level increased and decreased over the 71 day treatment period, with high measurements on days 15 and 71 of over 100 pmol/dL. Between 8 and 71 an increase of at least 1.5 fold was observed.

Table 5 presents the data for three subjects in Dose Group II, treated with 3 mg IFNτ three times daily. Baseline levels of blood OAS were taken on day of the study. Subject CLR/011 had a marginal response in terms of increased blood OAS level. Subject HCM/010 shows about a 1.5 fold increase in blood OAS level, and subject VCC/009 had a more than 4-fold increased in blood OAS level at test day 29.

The data in Tables 3–5 illustrate the varied response of individuals suffering from viral hepatitis C to oral IFNτ. Many patients had an increased blood OAS level, typically a 1.5 fold increase in blood OAS over initial baseline levels, often a two-fold increase, and in some cases, a four-fold increase. The response of each patient is dependent on a number of factors including the state of the infection and individualized bodily responses to treatment.

Accordingly, the invention contemplates administration of IFNτ orally to a patient in need of treatment, where the initial dose(s) of IFNτ is selected to achieve an increased blood OAS level for that particular patient. The IFNτ is administered in a form that targets the intestinal tract of the patient, rather than the oral cavity. Dosage selection can be made or confirmed, for example, by monitoring blood OAS or OAS mRNA levels e.g, prior to treatment and following initiation of treatment. Alternatively, an effective dose may be predetermined from model patient responses to given doses under different disease conditions. For example, a patient within a given age range and having a specified condition, e.g., HCV infection or MS, may be monitored for changes in blood OAS in response to different initial IFN-tau levels, to predetermine suitable doses for patients with that age/disease profile, and such dosing guidelines may be supplied to the treating physician. One aspect of the present invention includes an IFN-tau therapy kit that includes IFN-tau in an oral delivery form suitable for targeting the protein to the intestinal tract, e.g., an enteric coated form of IFN-tau, and product literature or insert that provides guidelines for effective doses, under different patient condition; that is, doses effective to produce a measurable increase in OAS blood levels. Preferably, the insert provides a range of doses and predicted initial changes in OAS response.

Following the initial administration, or when a dose is reached that produces a measurable increase in blood OAS levels (an effective dose), the administration of an effective dose IFNτ is continued, preferably on a daily or several-time-weekly basis, for an extended treatment period. The effective dose that is administered on an extended basis is one effective to produce an initial measurable increase in blood OAS, independent of the behavior of actual blood OAS levels over the extended treatment period, whether or not the continuing effective dose is the same or different from the initial effective dose. Thus, during the treatment period, blood OAS levels may remain constant at an elevated level, continue to increase, or even decrease (for example, in response to decreasing levels of infecting virus), even though the patient is continuing to receive an IFNτ dose effective to produce an initial measurable increase in blood OAS levels. This effective dose is typically between $10^5$ to $10^8$ units IFNτ/day, and can be adjusted to achieve a desired initial increase in blood OAS, e.g., between 1.5 and 4 fold normal, untreated levels.

Figure 7A:
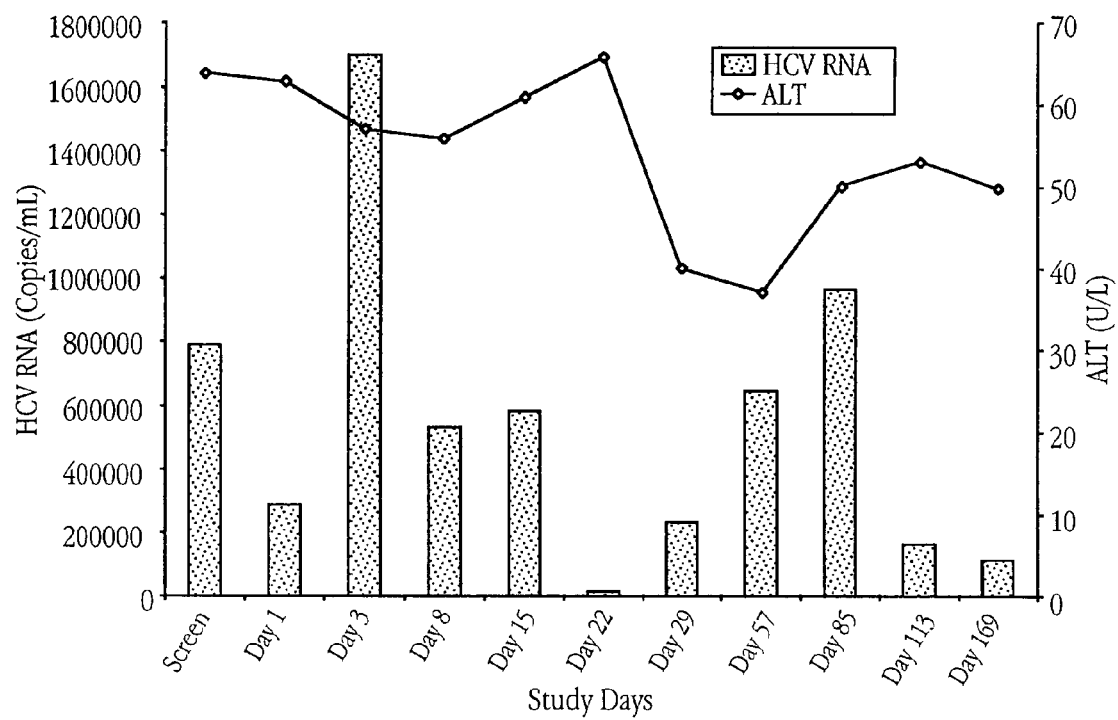
FIGS. 7A–7C show the hepatitis C (HCV) RNA and alanine aminotransferase (ALT) levels in three human patients following oral administration of $4.9 \times 10^8$ Units/day IFNτ.
Figure 7B:
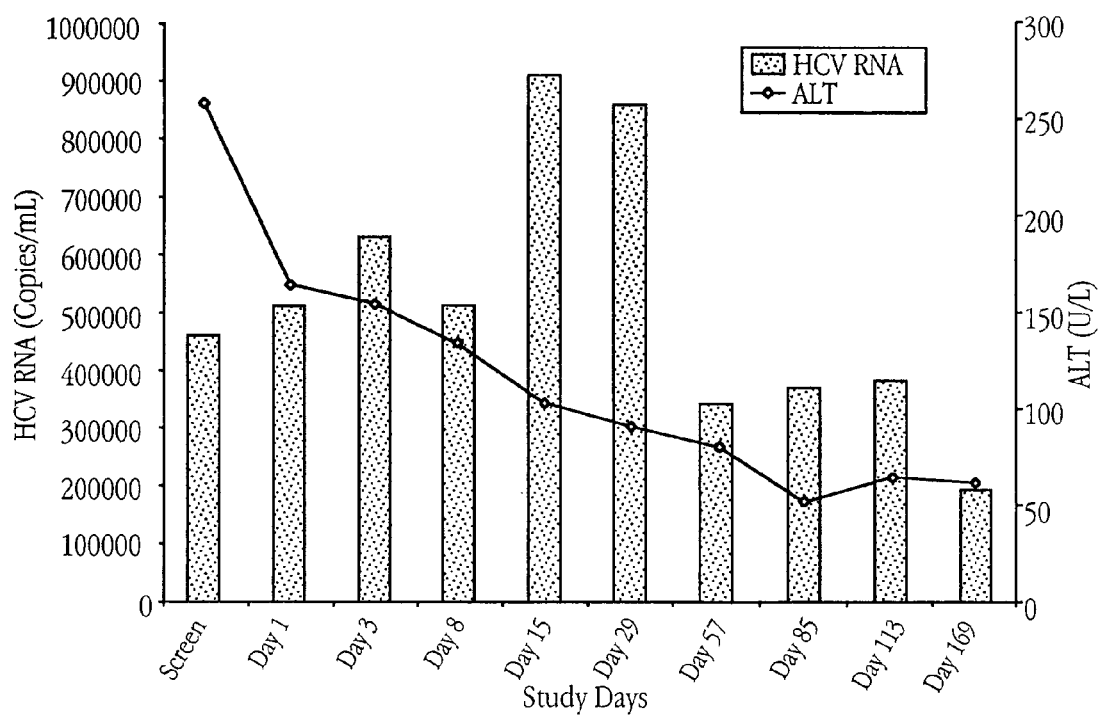
Figure 7C:
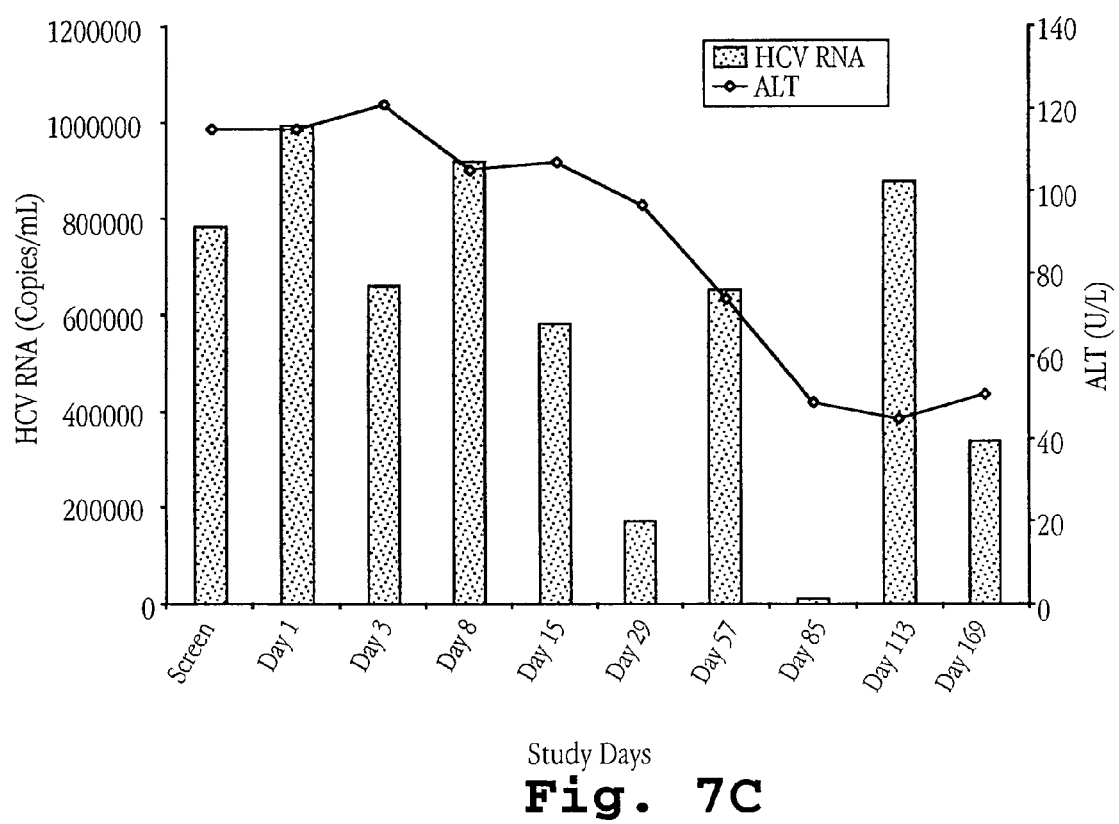

FIGS. 7–8 present the data for viral titer and alanine aminotransferase (ALT) levels for several of the patients in the study. Alanine aminotransferase is a serum enzyme that catalyzes the transfer of the γ-keto group of alanine to the γ-keto group of ketoglutarate, leading to the formation of oxaloacetic acid and pyruvic acid. ALT is found primarily in the liver, and patients suffering from a liver disease, such as hepatitis C, have an elevated ALT level in the blood (*HARRISON'S PRINCIPLES OF INTERNAL MEDICINE*, Wilson et al., Eds., 12$^{th}$ Editions, Part Nine, page 1309, (1991)). A healthy person has a serum ALT level of about 1–45 U/L. FIGS. 7A–7C show the hepatitis C (HCV) RNA viral titer (shaded bars) and alanine aminotransferase (ALT) levels (diamonds) in three patients in Dose Group I, patients PAB/001 (FIG. 7A), MSM/002 (FIG. 7B), and DMA/003 (FIG. 7C), following oral administration of 4.9×10$^8$ Units/day (0.33 mg t.i.d.) IFNτ. Patients MSM/002 and DMA/003 (FIGS. 7B, 7C) had a continual decrease in ALT level over the 169 day treatment period. Patient PAB/001 (FIG. 7A) showed a more varied ALT blood level with some increases, but had an overall decrease in ALT level as a result of IFNτ treatment.

Figure 8A:
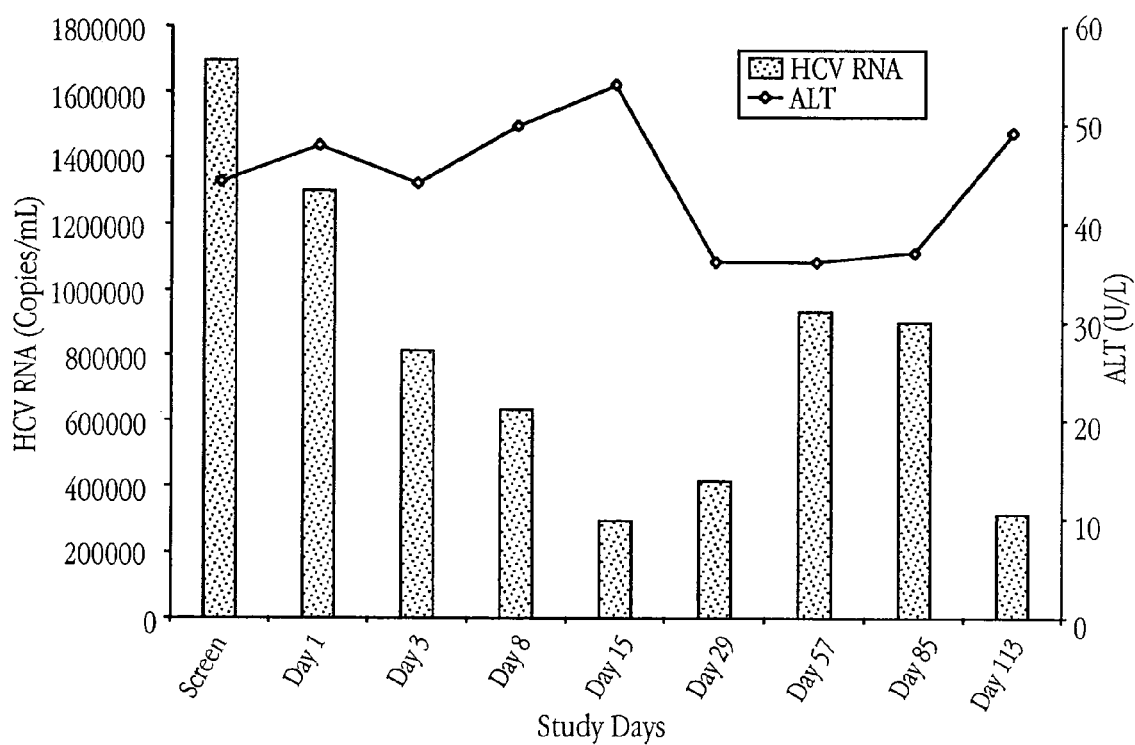
FIGS. 8A–8B show the hepatitis C (HCV) RNA and alanine aminotransferase (ALT) levels in two human patients following oral administration of $1.5 \times 10^9$ Units/day IFNτ.
Figure 8B:
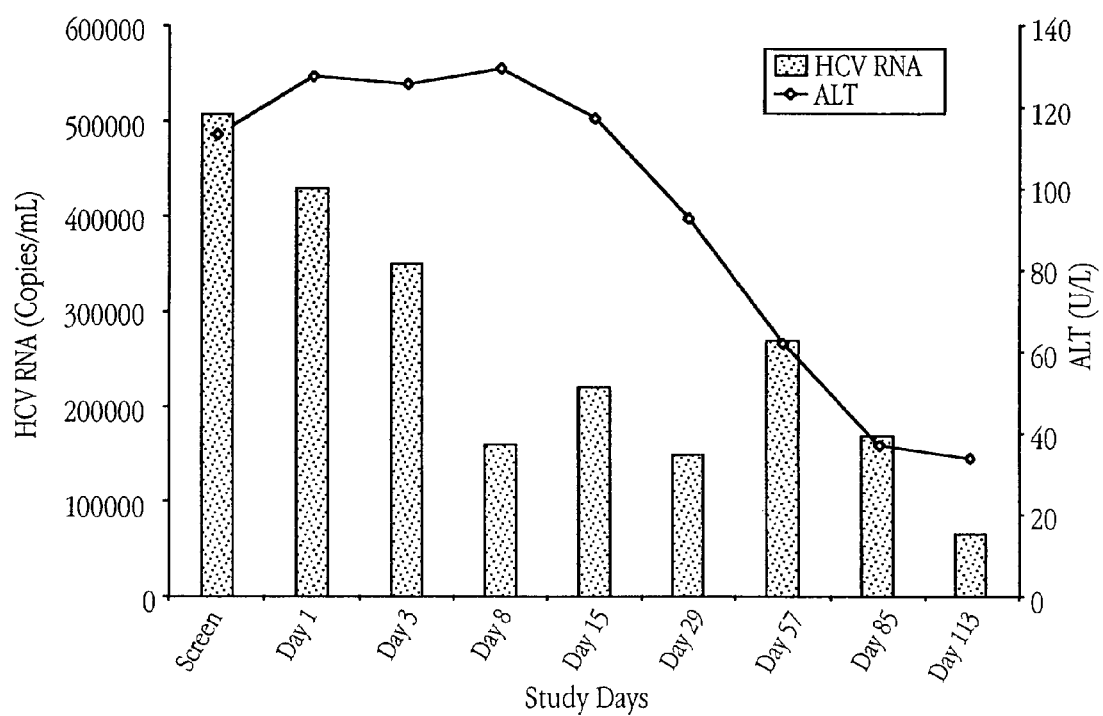

FIGS. 8A–8B show the hepatitis C (HCV) RNA and alanine aminotransferase (ALT) levels in patients AMC/007 (FIG. 8A) and VCC/009 (FIG. 8B) in Dose Group II, treated with 1.5×10$^9$ Units/day (1.0 mg t.i.d.) oral IFNτ. The two patients responded differently, with VCC/009 showing an initial increase in ALT in the first week of treatment, and then a continual decline in ALT level from about day 8 to day 113.

It will be appreciated that for some patients and for some conditions, administration of IFNτ in combination with another therapeutic agent is contemplated. For example, combination of IFNτ with other recognized hepatitis antiviral agents may be beneficial in some patients. More generally, combination of IFNτ with any known pharmaceutical agent is contemplated.

3. Administration of IFN to Mice with Experimental Allergic Encephalomyelitis

Oral administration of IFNτ for treatment of autoimmune disorders was illustrated in another study using a recognized model for multiple sclerosis. This study evaluates the efficacy of IFNτ in treating autoimmune disorders in general, by evaluating the response in rodents with experimental allergic encephalomyelitis (EAE; Zamvil, S. S. et al., *Ann. Rev. Immunol.*, 8:579–621 (1990)), an animal model of antigen-induced autoimmunity. EAE resembles human multiple sclerosis (MS) both in its clinical and pathological manifestations and can thus be used to assess treatments for human autoimmune diseases such as MS. EAE is a T-cell-mediated inflammatory autoimmune demyelinating disease induced by immunizing susceptible mouse, rat or guinea pig strains with myelin basic protein (MBP) or with encephalitogenic peptide fragments. Genetic susceptibility in the model animal strains is based in part on the capacity of encephalitogenic peptides to bind to particular class II major histocompatibility complex (MHC-II) molecules (Fritz, R. B., et al., *J. Immunol.* 130(3):1024–1026 (1983); Wraith, D. C., et al., *Cell* 59:247 (1989)). In particular, mice having the H-2$^u$ haplotype are susceptible to EAE. Susceptible mouse strains include PL/J mice (Klein, J., et al., *Immunogenetics* 17:553 (1983)), (PL/J×SJL)F$_1$ mice (Zamvil, S. S. et al., *Ann. Rev. Immunol.*, 8:579–621 (1990); Wraith, et al., 1989), B10.PL mice (Figuero, F., et al., *Immunogenetics* 15(4):399–404 (1982)), NZW mice (Kotzin, B. L., et al., *J. Exp. Med.* 265:1237 (1987)), and (NZB×NZW)F1 (Kotzin, B. L., et al., *J. Exp. Med.* 265:1237 (1987)) mice.

Studies conducted in support of the present invention and detailed below demonstrate that orally-administered IFNτ compositions are comparable in efficacy to injected IFNτ compositions with respect to the treatment of diseases or disease conditions which benefit from treatment with IFNτ. Not only was orally-administered IFNτ effective at treating a disease benefiting from IFNτ treatment (EAE), but the oral route of administration resulted in unexpected advantages relative to treatment with injected IFNτ compositions. For example, orally-administered IFNτ resulted in a significantly lower level of anti-IFNτ antibodies in the serum of treated individuals. This is beneficial because the orally-administered IFNτ is therefore less likely to be rendered ineffective by a host immune response (i.e., desensitization to the treatment and/or dose level is significantly decreased), and the individual receiving the treatment is less likely to suffer adverse side effects as a result of such an immune response.

Results of experiments demonstrating these and related findings are presented below.

a. Orally-Administered IFNτ Inhibits Development of EAE

As described in Example 5, orally-administered and injected IFNτ was tested for its ability to prevent the induction of EAE. EAE was induced in New Zealand White (NZW) mice by immunization with bovine myelin basic protein (bMBP). Recipient NZW mice received OvIFNτ by either i.p. injection or oral feeding 48 hours prior to, on the day of, and 48 hours after immunization with bovine myelin basic protein (bMBP) for induction of experimental allergic encephalomyelitis (EAE).

Both oral feeding and i.p. injection of OvIFNτ protected against EAE (Example 5, Table 6). All animals that received IFNτ via i.p. injection, and seven of nine animals that received IFNτ orally, were protected from symptoms of EAE. Furthermore, anti-OvIFNτ monoclonal antibody HL127 was effective at partially neutralizing the ability of the OvIFNτ to block EAE. These experiments demonstrate that orally-administered IFNτ is effective in treating symptoms of EAE, an animal model of multiple sclerosis.

b. OvIFNτ is Present in Sera Following Oral Administration.

To confirm that orally-administered IFNτ enters the circulation, the sera of mice that received IFNτ by i.p injection or by oral administration were tested for the presence of IFNτ using a cytopathic effect (antiviral) assay (Familetti, P. C. et al., *Meth. Enzymol.* 78:387 (1981)) as described in Example 6.

Figure 9:
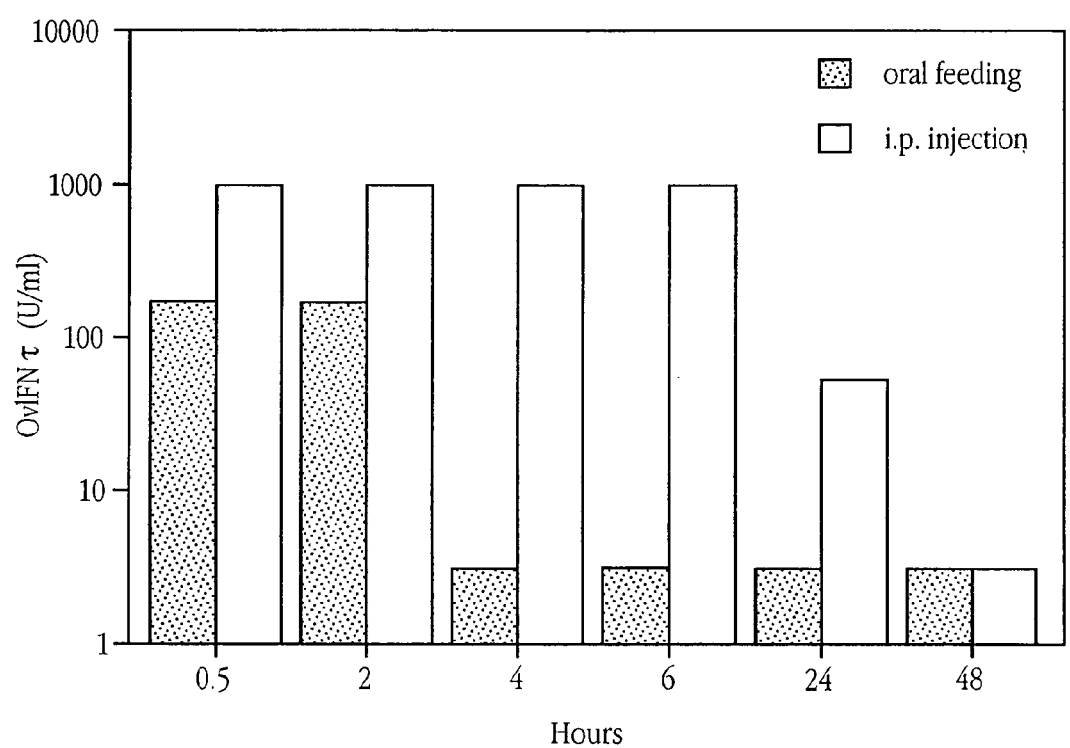
FIG. 9 shows the amount of IFNτ in NZW mouse sera after administration by either oral feeding (filled bars) or i.p. injection (open bars) as measured using an anti-viral assay.

The results are shown in FIG. 9. Specific activities are expressed in antiviral units/mg protein obtained from antiviral assays using MDBK cells. OvIFNτ was detected for up to two hours following oral feeding (filled bars) at levels of 200 U/mL. These data indicate that orally-administered IFNτ enters the circulation and remains in serum for about two hours after being administered.

c. Lack of Toxicity from Orally-Administered OvIFNτ

It has been previously demonstrated that the type I IFNs IFNα and IFNβ induced toxic side effects manifested as flu like symptoms, fever, nausea and malaise when used as therapeutics in humans (Degre, M., *Int. J. Cancer* 14:699 (1974); Fent, K. and G. Zbinden, *Trnds. Pharm. Sci.* 56:1–26 (1987)). In contrast, OvIFNτ exhibits a remarkable lack of toxicity both in vitro and in vivo. Studies performed in support of the present invention compared OvIFNτ with IFNs α and β for induction of toxicity as measured by lymphocyte depression in peripheral blood when given via oral feeding. Blood was obtained from the tail and white blood cells (WBC) counts were enumerated using a hemocytometer. Differential WBC counts were performed on Wright-Giemsa-stained blood smears.

The results are shown in Tables 1A, 1B, and 1C. Significant levels of toxicity were detected in mice fed either IFN α and β while no significant lymphocyte depression was detected in mice fed $10^5$, $2 \times 10^5$ or $5 \times 10^5$ U of OvIFNτ or PBS alone. These data suggest that orally-administered OvIFNτ has significantly-reduced toxicity with respect to other type I IFNs.

TABLE 1A

Comparison of IFNs τ, β and α for Toxicity After Oral Feeding

| IFN (DOSE) | CELL COUNT (CELL NO. × $10^3$) BEFORE ORAL FEEDING | |
|---|---|---|
| | TOTAL WBC | LYMPHOCYTES |
| PBS | 7.0 ± 1.4 | 6.1 ± 1.2 |
| τ($10^5$) | 7.5 ± 0.7 | 6.4 ± 0.6 |
| τ(2 × $10^5$) | 6.5 ± 1.2 | 5.3 ± 0.6 |
| τ(5 × $10^5$) | 7.5 ± 0.7 | 6.5 ± 0.6 |
| β($10^5$) | 7.0 ± 0.7 | 5.9 ± 1.2 |
| β(2 × $10^5$) | 7.5 ± 2.1 | 6.5 ± 1.8 |
| α($10^5$) | 7.5 ± 0.7 | 6.6 ± 0.6 |

TABLE 1B

Comparison of IFNs τ, β and α for Toxicity After Oral Feeding

| IFN (DOSE) | CELL COUNT (CELL NO. × $10^3$) 18 H AFTER ORAL FEEDING | | |
|---|---|---|---|
| | TOTAL WBC | LYMPHOCYTES | % LYMPHOCYTE DEPRESSION |
| PBS | — | — | — |
| τ($10^5$) | 7.0 ± 1.4 | 6.0 ± 1.3 | 6.2 |
| τ(2 × $10^5$) | 7.0 ± 2.8 | 5.9 ± 2.4 | 0 |
| τ(5 × $10^5$) | 7.5 ± 2.1 | 6.3 ± 1.8 | 3.1 |
| β($10^5$) | 6.5 ± 0.7 | 5.1 ± 0.6 | 13.6 |
| β(2 × $10^5$) | 6.5 ± 0.7 | 4.1 ± 0.4† | 37.0 |
| α($10^5$) | 6.5 ± 2.1 | 4.7 ± 1.6 | 28.8 |

†p<0.05

TABLE 1C

Comparison of IFNs τ, β and α for Toxicity After Oral Feeding

| IFN (DOSE) | CELL COUNT (CELL NO. × $10^3$) 24 H AFTER ORAL FEEDING | | |
|---|---|---|---|
| | TOTAL WBC | LYMPHOCYTES | % LYMPHOCYTE DEPRESSION |
| PBS | 7.5 ± 0.7 | 6.4 ± 0.6 | 0 |
| τ($10^5$) | 8.0 ± 2.8 | 6.9 ± 2.4 | 0 |
| τ(2 × $10^5$) | 7.0 ± 1.4 | 6.0 ± 1.1 | 0 |
| τ(5 × $10^5$) | 8.0 ± 4.2 | 7.0 ± 3.6 | 0 |
| β($10^5$) | 6.5 ± 3.5 | 5.1 ± 2.8 | 13.6 |
| β(2 × $10^5$) | 6.5 ± 0.7 | 4.0 ± 0.4† | 38.5 |
| α($10^5$) | 7.0 ± 0 | 5.0 ± 0‡ | 24.2 |

†p<0.05
‡p<0.03 d. OvIFNτ Prevents Chronic Relapse of EAE

Figure 10A:
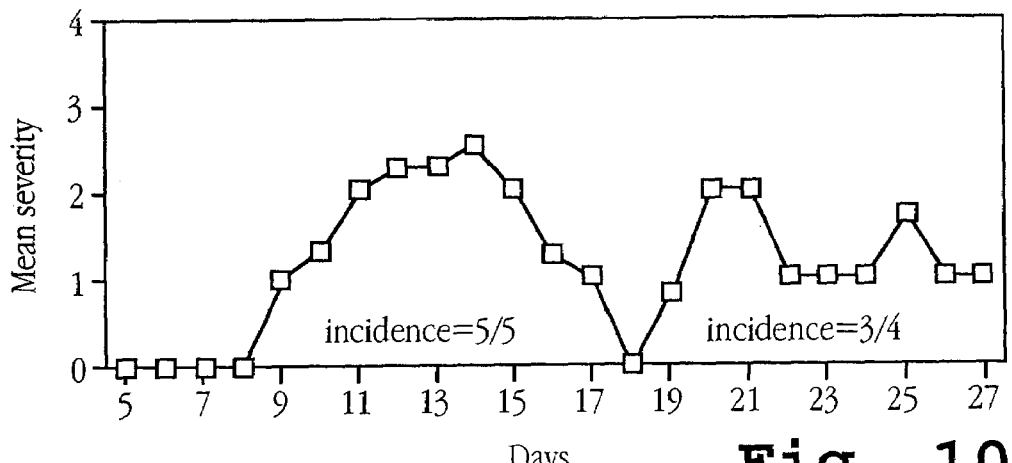
FIGS. 10A–10C show the prevention of chronic-relapsing experimental allergic encephalomyelitis (EAE) in SJL mice by orally-administered (FIG. 10C) and i.p.-injected (FIG. 10B) IFNτ as compared with mice receiving no treatment (FIG. 10A).
Figure 10B:
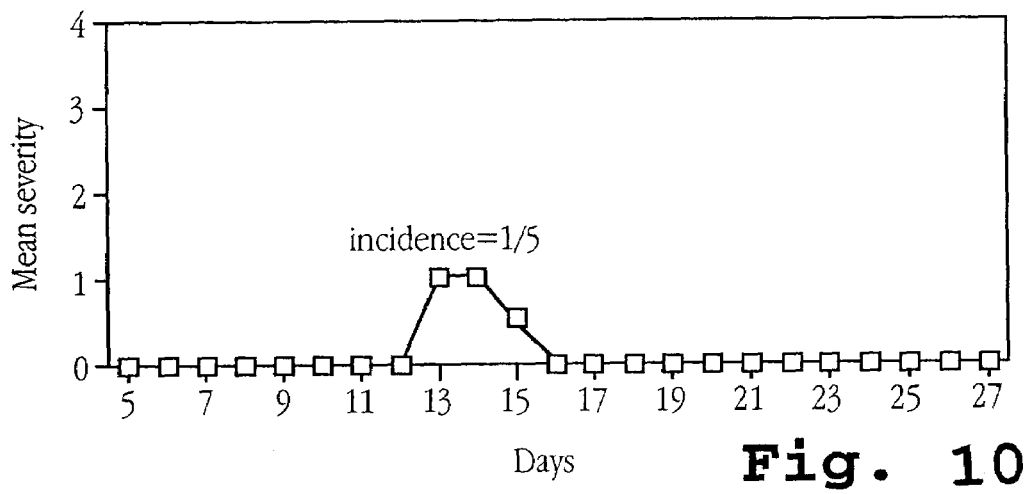
Figure 10C:
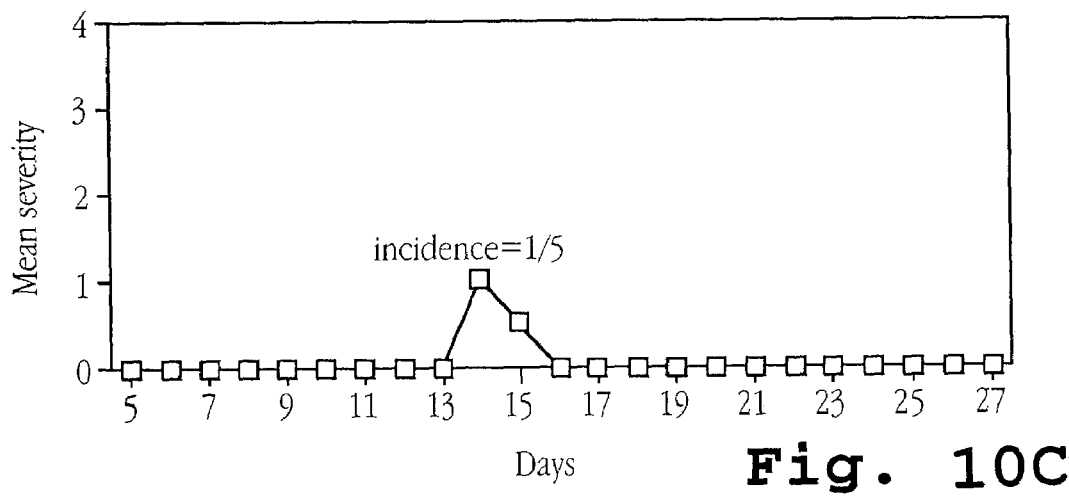

In addition to preventing the onset of symptoms associated with EAE, orally-administered OvIFNτ prevents paralysis in a chronic-relapsing model of EAE, as detailed in Example 7. Whereas 5/5 mice immunized with MBP (to induce EAE) which did not receive OvIFNτ treatment developed chronic relapsing paralysis, 4/5 animals treated with OvIFNτ (either i.p. injection or oral feeding, administered every 48 hours) were fully protected from the disease (FIGS. 10B and 10C). These data further support the results described above, and indicate that oral administration of IFNτ can block the development of chronic relapsing EAE. The studies also suggest that orally-administration of IFNτ as infrequently as once every 48 hours, over an extended period of time, is as effective as i.p. injection at treating a disease condition responsive to treatment by IFNτ.

e. Histological Analyses of Spinal Cord from EAE Mice following Oral Administration of IFNτ.

Figure 11A:
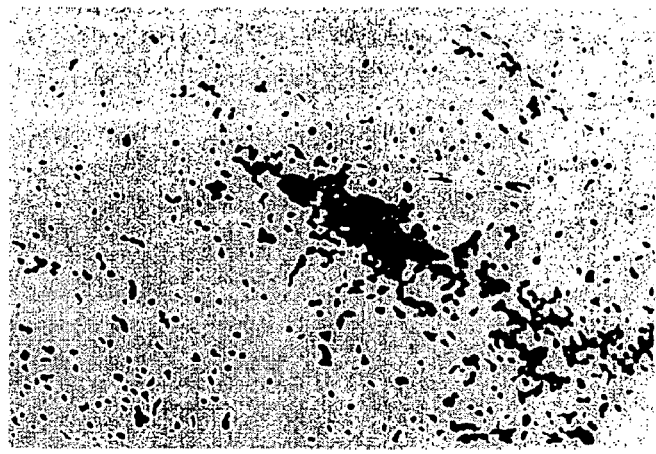
FIGS. 11A–11C show sections of mouse spinal cord stained with cresyl violet for detection of lymphocyte infiltration from EAE-induced animals receiving either no IFNτ treatment (FIG. 11A), IFNτ treatment by i.p. injection (FIG. 11B), or IFNτ treatment by oral feeding (FIG. 11C).
Figure 11B:
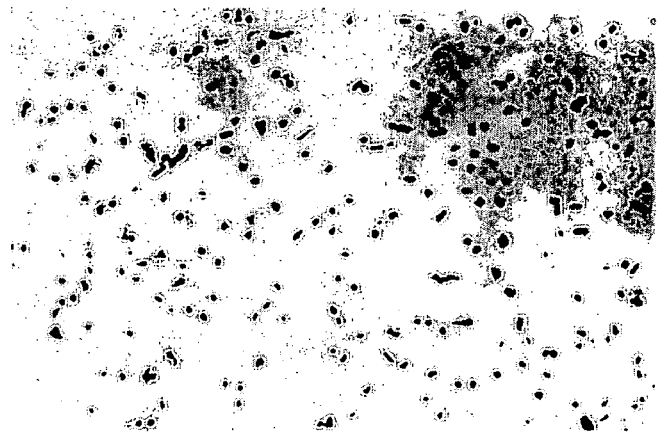
Figure 11C:
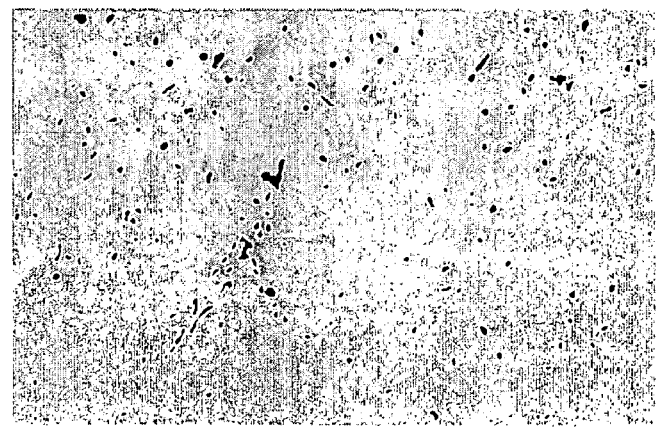

The ability of OvIFNτ to prevent EAE was also assayed by analyzing the effect of OvIFNτ treatment on cellular consequences of the disease, manifested in the central nervous system (CNS) as lymphocytic lesions in spinal cord white matter. The lesions are indicative of the extent of lymphocyte infiltration into the CNS. MBP-immunized mice were either not treated (control) or treated with OvIFNτ by oral or i.p. routes, and sections of the spinal cord lumbar region were stained and evaluated for lymphocytes as described in Example 8. Photomicrographs of the tissue sections are shown in FIGS. 11A–11C. Lymphocytic lesions were present in spinal cord white matter of control animals (FIG. 11A), but not in mice treated with OvIFNτ by i.p. injection (FIG. 11B) or oral feeding (FIG. 11C). These data indicate that the protective effect of IFNτ is associated with inhibition of lymphocyte infiltration of the CNS. Further, the data demonstrate that IFNτ treatment inhibits cellular manifestation of the autoimmune disease, rather than simply masking symptoms.

f. Cessation of Treatment with OvIFNτ Results in Relapsing Paralysis.

Figure 13:
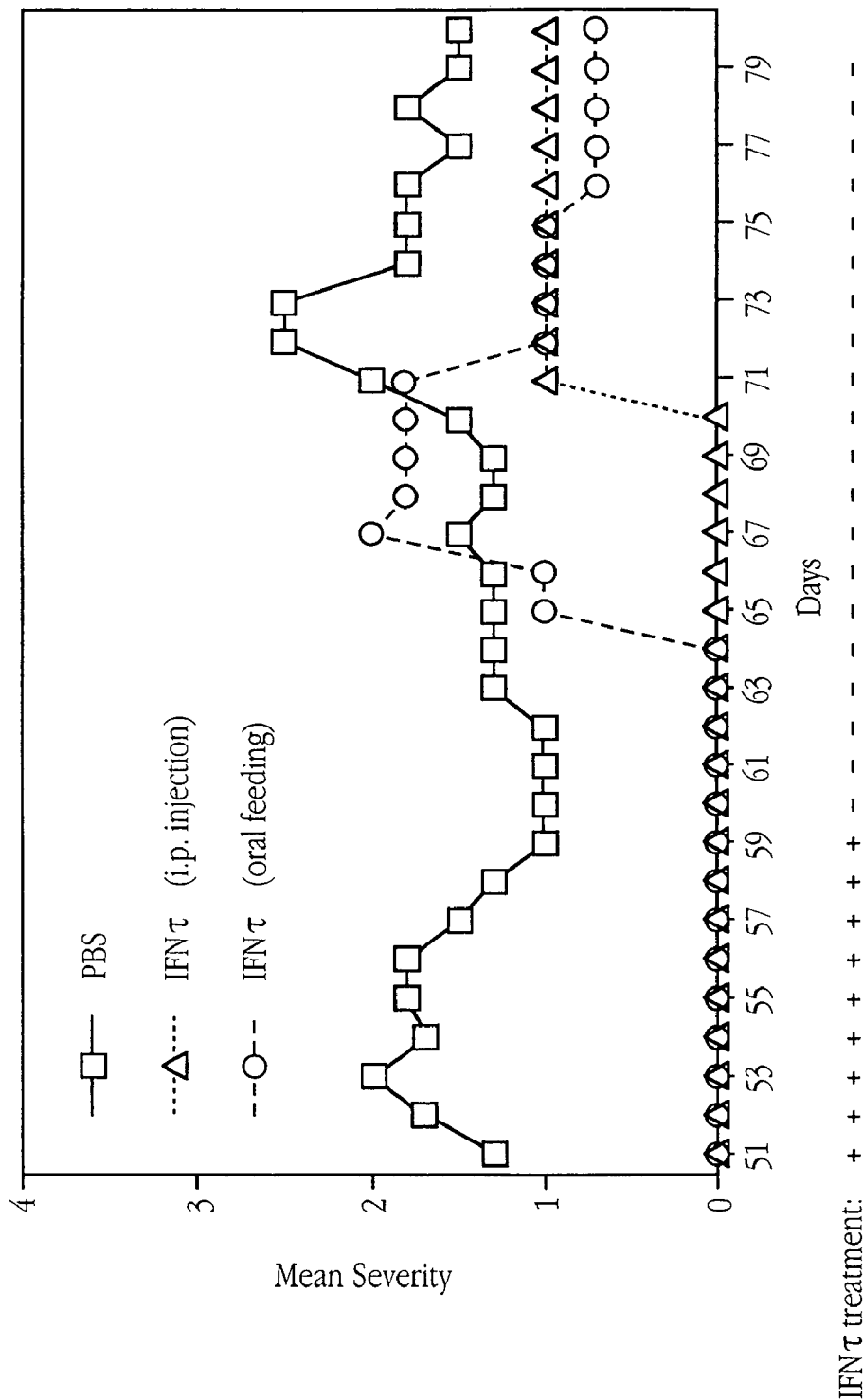
FIG. 13 shows relapse of EAE in SJL mice following removal of IFNτ treatment.

Example 10 describes a study performed to determine the type and duration of treatment effective to prevent EAE in mice injected with MBP, and the results are shown in FIG. 13. The mice were protected from EAE by OvIFNτ treatment via i.p. injection or oral feeding (every 48 hours) as long as the treatment persisted (58 days in Example 10), but developed symptoms of the disease after OvIFNτ treatment was stopped (FIG. 13). These results suggest that while IFNτ may not cure an autoimmune condition like EAE (e.g., MS), it is an effective treatment that inhibits the pathological manifestations of the condition so long as treatment is continued.

g. Oral Administration of OvIFNτ Reduces Anti-OvIFNτ Antibody Response.

As detailed in Example 11, one advantage of orally-administered (as opposed to injected) IFNτ treatment is a reduction in the anti-IFNτ antibody titer in individuals receiving the oral treatment. After removal of OvIFNτ treatment, mice from each treatment group were bled and sera were examined for the presence of anti-OvIFNτ antibodies by ELISA. Whereas mice receiving IFNτ by i.p. injection exhibited elevated levels of anti-IFNτ antibodies, animals receiving IFNτ by oral feeding exhibited much lower anti-IFNτ antibody titers (typically 3 to 5-fold lower). As expected, mice which received no OvIFNτ treatment displayed no anti-OvIFNτ antibodies.

The sera were also examined for their ability to neutralize OvIFNτ antiviral activity on the MDBK cell line. None of the sera from either i.p. injected or orally fed mice possessed neutralizing activity (Table 7). These results suggest that oral feeding of OvIFNτ largely circumvents an antibody response directed against the OvIFNτ protein. Such a reduced antibody response in orally-treated subjects reduces the chance of undesirable immune system-related side effects of IFNτ treatment.

III. Methods of Use

In a first aspect, the invention provides a method for treating in a human subject a disease or condition responsive to interferon therapy. A condition "responsive to interferon therapy" is one in which the existence, progression, or symptoms of the condition is altered upon administration of an interferon, in particular a type-I interferon, and more particularly, interferon-tau. Conditions responsive to treatment with IFNα or IFNβ may also respond to treatment with IFNτ. More preferably, a condition responsive to interferon therapy is one where the existence, progression, or symptoms of the condition are alleviated by IFNτ administered in a non-oral route, such as injection. The method described herein encompasses providing IFNτ in an orally-administrable dosage form, for administration to the stomach and/or intestines, in an amount effective for therapy, as evidenced by an increase in the subject's blood OAS levels.

IFNτ has biological activity as an antiviral agent, an anti-proliferative agent, and in treatment of autoimmune disorders (see for example U.S. Pat. Nos. 5,958,402; 5,942,223; 6,060,450; 6,372,206, which are incorporated by reference herein). Accordingly, the invention contemplates oral administration of IFNτ for treatment of any condition responsive to IFN-τ when administered via injection. Conditions and diseases which may be treated using methods of the present invention include autoimmune, inflammatory, proliferative and hyperproliferative diseases, as well as immunologically-mediated diseases.

A. Treatment of Immune System Disorders

The method of the present invention is advantageous for treating conditions relating to immune system hypersensitivity. There are four types of immune system hypersensitivity (Clayman, C. B., Ed., AMERICAN MEDICAL ASSOCIATION ENCYCLOPEDIA OF MEDICINE, Random House, New York, N. Y., (1991)). Type I, or immediate/anaphylactic hypersensitivity, is due to mast cell degranulation in response to an allergen (e.g., pollen), and includes asthma, allergic rhinitis (hay fever), urticaria (hives), anaphylactic shock, and other illnesses of an allergic nature. Type II, or autoimmune hypersensitivity, is due to antibodies that are directed against perceived "antigens" on the body's own cells. Type III hypersensitivity is due to the formation of antigen/antibody immune complexes which lodge in various tissues and activate further immune responses, and is responsible for conditions such as serum sickness, allergic alveolitis, and the large swellings that sometimes form after booster vaccinations. Type IV hypersensitivity is due to the release of lymphokines from sensitized T-cells, which results in an inflammatory reaction. Examples include contact dermatitis, the rash of measles, and "allergic" reactions to certain drugs.

The mechanisms by which certain conditions may result in hypersensitivity in some individuals are generally not well understood, but may involve both genetic and extrinsic factors. For example, bacteria, viruses or drugs may play a role in triggering an autoimmune response in an individual who already has a genetic predisposition to the autoimmune disorder. It has been suggested that the incidence of some types of hypersensitivity may be correlated with others. For example, it has been proposed that individuals with certain common allergies are more susceptible to autoimmune disorders.

Autoimmune disorders may be loosely grouped into those primarily restricted to specific organs or tissues and those that affect the entire body. Examples of organ-specific disorders (with the organ affected) include multiple sclerosis (myelin coating on nerve processes), type I diabetes mellitus (pancreas), Hashimotos thyroiditis (thyroid gland), pernicious anemia (stomach), Addison's disease (adrenal glands), myasthenia gravis (acetylcholine receptors at neuromuscular junction), rheumatoid arthritis (joint lining), uveitis (eye), psoriasis (skin), Guillain-Barré Syndrome (nerve cells) and Grave's disease (thyroid). Systemic autoimmune diseases include systemic lupus erythematosus and dermatomyositis.

Other examples of hypersensitivity disorders include asthma, eczema, atopical dermatitis, contact dermatitis, other eczematous dermatitides, seborrheic dermatitis, rhinitis, Lichen planus, Pemplugus, bullous Pemphigoid, Epidermolysis bullosa, uritcaris, angioedemas, vasculitides, erythemas, cutaneous eosinophilias, Alopecia areata, atherosclerosis, primary biliary cirrhosis and nephrotic syndrome. Related diseases include intestinal inflammations, such as Coeliac disease, proctitis, eosinophilia gastroenteritis, mastocytosis, inflammatory bowel disease, Chrohn's disease and ulcerative colitis, as well as food-related allergies.

Autoimmune diseases particularly amenable for treatment using the methods of the present invention include multiple sclerosis, type I (insulin dependent) diabetes mellitus, lupus erythematosus, amyotrophic lateral sclerosis, Crohn's disease, rheumatoid arthritis, stomatitis, asthma, uveitis, allergies and psoriasis.

The method of the present invention is used to therapeutically treat and thereby alleviate autoimmune disorders, such as those discussed above. Treatment of an autoimmune disorder is exemplified herein with respect to the treatment of EAE, an animal model for multiple sclerosis. When used to treat an autoimmune disorder, IFNτ is administered at a dose sufficient to achieve the measurable increase in OAS during the initial phase(s) of IFNτ administration. Once a desired effective dose is achieved, the patient is treated over an extended period with an effective IFNτ dose, independent of further changes in OAS blood levels. The treatment period extends at least over the period of time when the patient is symptomatic. Upon cessation of symptoms associated with the autoimmune condition, the dosage may be adjusted downward or treatment may cease. The patient may be co-treated during the treatment period of IFNτ treatment with another agent, such as a known anti-inflammatory or immune-suppressive agent.

B. Treatment of Viral Infections

The method of the invention is also used to treat conditions associated with viral infection. The antiviral activity of IFNτ has broad therapeutic applications without the toxic effects that are usually associated with IFNαs, and IFNτ exerts its therapeutic activity without adverse effects on the cells. The relative lack of cytotoxicity of IFNτ makes it extremely valuable as an in vivo therapeutic agent and sets IFNτ apart from most other known antiviral agents and all other known interferons.

Formulations containing IFNτ can be orally-administered to inhibit viral replication. For use in treating a viral infection, the protein is administered at a dose sufficient to achieve a measurable increase in blood OAS in the patient. Thereafter, treatment is continued at an effective dose, independent of further changes in blood OAS levels, for example, a fall in OAS blood levels due to reduction in viral load. Administration of IFNτ is continued until the level of viral infection, as measured for example from a blood viral titer or from clinical observations of symptoms associated with the viral infection, is reduced. Examples of specific viral diseases which may be treated by orally-administered IFNτ include, but are not limited to, hepatitis A, hepatitis B, hepatitis C, non-A, non-B, non-C hepatitis, Epstein-Barr viral infection, HIV infection, herpes virus (EB, CML, herpes simplex), papilloma, poxvirus, picorna virus, adeno virus, rhino virus, HTLV I, HTLV II, and human rotavirus. The patient may be co-treated during the treatment period with a second antiviral agent, as a nucleoside analog, antisense agent, or the like.

C. Method for Treating Conditions of Cellular Proliferation

In another embodiment, the methods of the invention are contemplated for treatment of conditions characterized by hyperproliferation. IFNτ exhibits potent anticellular proliferation activity. Accordingly, a method of inhibiting cellular growth by orally administering IFNτ is contemplated, in order to inhibit, prevent, or slow uncontrolled cell growth.

Examples of specific cell proliferation disorders which may be treated by orally-administered IFNτ include, but are not limited to, hairy cell leukemia, Kaposi's Sarcoma, chronic myelogenous leukemia, multiple myeloma, superficial bladder cancer, skin cancer (basal cell carcinoma and malignant melanoma), renal cell carcinoma, ovarian cancer, low grade lymphocytic and cutaneous T cell lymphoma, and glioma.

For use in treating treating a cell-proliferation condition, IFNτ is administered at a dose sufficient to achieve an initial measurable increase in blood OAS in the patient. Thereafter, treatment is continued at an effective dose, independent of further changes in blood OAS levels, for example, a fall in OAS blood levels due to a reduction in cancer cells in the body. Administration of IFNτ at an effective dose is continued until a desired level of regression is observed, as measured for example, by tumor size or extent of cancer cells in particular tissues. The patient may be co-treated during the treatment period with a second anticancer agent, e.g., cis-platin, doxorubicin, or taxol.

D. Formulations and Dosages

Oral preparations containing IFNτ can be formulated according to known methods for preparing pharmaceutical compositions. In general, the IFNτ therapeutic compositions are formulated such that an effective amount of the IFNτ is combined with a suitable additive, carrier and/or excipient in order to facilitate effective oral administration of the composition. For example, tablets and capsules containing IFNτ may be prepared by combining IFNτ (e.g., lyophilized IFNτ protein) with additives such as pharmaceutically acceptable carriers (e.g., lactose, corn starch, microcrystalline cellulose, sucrose), binders (e.g., alpha-form starch, methylcellulose, carboxymethylcellulose, hydroxypropylcellulose, hydroxypropylmethylcellulose, polyvinylpyrrolidone), disintegrating agents (e.g., carboxymethylcellulose calcium, starch, low substituted hydroxy-propylcellulose), surfactants (e.g., Tween 80, polyoxyethylene-polyoxypropylene copolymer), antioxidants (e.g., L-cysteine, sodium sulfite, sodium ascorbate), lubricants (e.g., magnesium stearate, talc), or the like.

Further, IFNτ polypeptides of the present invention can be mixed with a solid, pulverulent or other carrier, for example lactose, saccharose, sorbitol, mannitol, starch, such as potato starch, corn starch, millopectine, cellulose derivative or gelatine, and may also include lubricants, such as magnesium or calcium stearate, or polyethylene glycol waxes compressed to the formation of tablets. By using several layers of the carrier or diluent, tablets operating with slow release can be prepared.

Liquid preparations for oral administration can be made in the form of elixirs, syrups or suspensions, for example solutions containing from about 0.1% to about 30% by weight of IFNτ, sugar and a mixture of ethanol, water, glycerol, propylene, glycol and possibly other additives of a conventional nature.

Another suitable formulation is a protective dosage form that protects the protein for survival in the stomach and intestines until absorbed by the intestinal mucosa. Protective dosage forms for proteins are known in the art, and include enteric coatings and/or mucoadhesive polymer coatings. Exemplary mucoadhesive polymer formulations include ethyl cellulose, hydroxypropylmethylcellulose, Eudragit®, carboxyvinyl polymer, carbomer, and the like. A dosage form designed for administration to the stomach via ingestion for delivery of IFNτ in an active form to the intestinal tract, and particularly to the small intestine, is contemplated. Alternatively, IFNτ can be co-administered with protease inhibitors, stabilized with polymeric materials, or encapsulated in a lipid or polymer particle to offer some protection from the stomach and/or intestinal environment.

An orally-active IFNτ pharmaceutical composition is administered in a therapeutically-effective amount to an individual in need of treatment. The dose may vary considerably and is dependent on factors such as the seriousness of the disorder, the age and the weight of the patient, other medications that the patient may be taking and the like. This amount or dosage is typically determined by the attending physician. The dosage will typically be between about $1 \times 10^4$ and $1 \times 10^9$ units/day, more preferably between $1 \times 10^5$ and $1 \times 10^8$ units/day, preferably between about $1 \times 10^6$ and $1 \times 10^7$ units/day. In one specific embodiment, IFN-τ is administered orally at a dosage of greater than about $1 \times 10^4$ units/day, preferably of greater than about $1 \times 10^5$ units/day, more preferably of greater than about $1 \times 10^6$ units/day, and still more preferably greater than about $1 \times 10^8$ units/day.

Disorders requiring a steady elevated level of IFNτ in plasma will benefit from administration as often as about every two to four hours, while other disorders, such as multiple sclerosis, may be effectively treated by administering a therapeutically-effective dose at less frequent intervals, e.g., once a day or once every 48 hours. The rate of administration of individual doses is typically adjusted by an attending physician to enable administration of the lowest total dosage while alleviating the severity of the disease being treated. As discussed above, the method contemplates administering IFNτ orally at a first dose to a patient in need of treatment, and monitoring a biological marker to determine the individual patient response to the first dosage level. Monitoring can be readily done via a blood draw and analysis of a marker, such as OAS enzyme in the blood, using, for example, a radioimmunoassay kit. Monitoring can also be done via a blood draw and analysis of mRNA expression levels of OAS in cells, such as in blood lymphocytes. Accordingly, in another aspect, the invention contemplates a kit for using in treating a person suffering from a condition responsive to IFNτ. The kit includes a first part, comprised of a container containing one or more dosage form units designed for oral administration of IFNτ and a second part comprised of components required to monitor a biomarker of IFNτ, such as the components needed to analyze blood OAS enzyme or mRNA levels.

Once improvement of a patient's condition has occurred, a maintenance dose is administered if necessary. Subsequently, the dosage or the frequency of administration, or both, may be reduced, as a function of the symptoms, to a level at which the improved condition is retained.

It will, of course, be understood that the oral administration of IFNτ in accord with the invention may be used in combination with other therapies. For example, IFNτ can be accompanied by administration of an antigen against which an autoimmune response is directed. Examples include co-administration of myelin basic protein and IFNτ to treat multiple sclerosis; collagen and IFNτ to treat rheumatoid arthritis, and acetylcholine receptor polypeptides and IFNτ to treat myasthenia gravis.

Furthermore, IFNτ may be orally administered with known immunosuppressants, such as steroids, to treat autoimmune diseases such as multiple sclerosis. The immunosuppressants may act synergistically with IFNτ and result in a more effective treatment that could be obtained with an equivalent dose of IFNτ or the immunosuppressant alone.

Similarly, in a treatment for a cancer or viral disease, IFNτ may be administered in conjunction with, e.g., a therapeutically effective amount of one or more chemotherapy agents such as busulfan, 5-fluorouracil (5-FU), zidovudine (AZT), leucovorin, melphalan, prednisone, cyclophosphamide, dacarbazine, cisplatin, dipyridamole, and the like.

IV. EXAMPLES

The following examples further illustrate the invention described herein and are in no way intended to limit the scope of the invention.

Materials and Methods

A. Production of IFNτ

In one embodiment, a synthetic IFNτ gene was generated using standard molecular methods (Ausubel, et al., 1988) by ligating oligonucleotides containing contiguous portions of a DNA sequence encoding the IFNτ amino acid sequence. The DNA sequence used may be either SEQ ID NO:1 or 4 or the sequence as shown in Imakawa, et al., 1987. The resulting IFNτ polynucleotide coding sequence may span position 16 through 531: a coding sequence of 172 amino acids.

In one embodiment, the full length synthetic gene StuI/SStI fragment (540 bp) may be cloned into a modified pIN III omp-A expression vector and transformed into a competent SB221 strain of E. coli. For expression of the IFNτ protein, cells carrying the expression vector were grown in L-broth containing ampicillin to an OD (550 nm) of 0.1–1, induced with IPTG (isopropyl-1-thio-b-D-galactoside) for 3 hours and harvested by centrifugation. Soluble recombinant IFN-τ may be liberated from the cells by sonication or osmotic fractionation.

For expression in yeast, the IFN-τ gene may amplified using polymerase chain reaction (PCR; Mullis, K. B., U.S. Pat. No. 4,683,202, issued 28 Jul. 1987; Mullis, K. B., et al., U.S. Pat. No. 4,683,195, issued 28 Jul. 1987) with PCR primers containing StuI and SacI restriction sites at the 5' and 3' ends, respectively. The amplified fragments were digested with StuI and SacII and ligated into the SacII and SmaI sites of pBLUESCRIPT+(KS), generating pBSY-IFNτ. Plasmid pBSY-IFNτ was digested with SacI and EcoRV and the fragment containing the synthetic IFN-τ gene was isolated. The yeast expression vector pBS24Ub (Ecker, D. J., et al., J. Biol. Chem. 264:7715–7719 (1989)) was digested with SalI. Blunt ends were generated using T4 DNA polymerase. The vector DNA was extracted with phenol and ethanol precipitated (Sambrook, J., et al., in MOLECULAR CLONING: A LABORATORY MANUAL, Second Edition, Cold Spring Harbor Laboratory, Cold Spring Harbor, N.Y. (1989)). The recovered plasmid was digested with SacII, purified by agarose gel electrophoresis, and ligated to the SacII-EcoRV fragment isolated from pBSY-IFN-τ. The resulting recombinant plasmid was designated pBS24Ub-IFNτ.

The recombinant plasmid pBS24Ub-IFNτ was transformed into E. coli. Recombinant clones containing the IFN-τ insert were isolated and identified by restriction enzyme analysis. IFN-τ coding sequences were isolated from pBS24Ub-IFNτ and cloned into a Pichia pastoris vector containing the alcohol oxidase (AOX1) promoter (Invitrogen, San Diego, Calif.). The vector was then used to transform Pichia pastoris GS115 His⁻ host cells and protein was expressed following the manufacturer's instructions. The protein was secreted into the medium and purified by successive DEAE-cellulose and hydroxyapatite chromatography to electrophoretic homogeneity as determined by SDS-PAGE and silver staining.

In one embodiment, the purified IFN-τ protein has a specific activity of about 0.29 to about $0.44 \times 10^8$ U/mg as measured by anti-viral activity on Madin-Darby bovine kidney (MDBK) cells. In another embodiment, the protein has a specific activity of about $4.9 \times 10^8$ U/mg as measured by the anti-viral activity bioassay.

Example 1

Induction of OAS with Orally and Intraperitoneally Administered Ovine IFN-τ to Mice IFNτ ($4.99 \times 10^8$ units/mg protein; Pepgen Corp., California or Biological Process Development Facility, Dept. of Food Science and Technology, University of NE-Lincoln, Lincoln, Nev.; SEQ ID NO:4) was dissolved in 10% maltose solution to prepare IFNτ solution. The use of IFNτ (SEQ ID NO:2) is also contemplated in the present invention. Two hundred microliters of IFNτ solution was orally administered to ICR mice (average body weight approximately 30 g, 6 weeks of age, female) using a 20 gauge disposable oral sound (Fuchigami, Kyoto) to inject directly to an upper part of the stomach (gastric administration; GA).

For intraperitoneal administration (i.p.), 100 microliters of IFNτ solution was used. Sample injection to an upper part of a stomach was confirmed by administration of a dye. Twenty-four hours after the administration, the mouse was anesthetized with nembutal. Blood was taken from a heart of the mouse and an OAS activity in whole blood was determined by 2-5A RIA Kit (Eiken Chemical, Tokyo; Shindo, M. et al., Hepatology, 9:715–719 (1989)).

The results are shown in FIG. 1.

Example 2

Dose-Dependent Induction of OAS by Oral Administration of IFN-τ in Mice

Using the same procedure as Example 1, IFNτ was orally administered in units of 0, $10^3$, $10^4$, or $10^5$ to an ICR mouse. Twelve hours after oral administration, whole blood was taken from a mouse heart and an OAS activity of whole blood was determined. The results are shown in FIG. 2.

Example 3

Administration of IFNτ to Mice

Pathogen-free 5-week-old female mice of the ICR, BALB/c, C57BL/9, NZW/N and SJL/J strains were purchased from Japan SLC. Inc., Hamamatsu. The mice were reared one week in the laboratory before experiments.

Recombinant ovine IFN-τ (IFN-τ) having a sequence identified herein as SEQ ID NO:3 was obtained (Pepgen Corporation, Alameda, Calif.). The preparation used in this study had a specific activity of $5 \times 10^8$ units (U)/mg protein as assayed in MDBK cells challenged with VSV and standardized against human IFN-α. Natural murine IFN-α (MuIFN-α) was supplied by Sumitomo Pharmaceutical Co. (Osaka, Japan), whose specific activity was $1 \times 10^8$ international units (IU)/mg protein.

For administration to the mice, IFN-τ was dissolved in a solution containing 10% maltose. Samples of 0.2 ml were administered to mice (6-week-old females) by either peroral (p.o.) treatment or intraperitoneal (i.p.) injection. When given orally, the samples were introduced directly into the upper part of the stomach using a 20 gauge oral feeding needle. Before the administration, mice were deprived of both food and drink for 6 hours, starting at 1 pm and ending at 7 pm. After the fasting, IFNτ was administered by either the p.o. or i.p. route and food and drink were given at 6 hours. Then, whole blood was obtained from the heart at 24 hours.

The 2',5'-oligoadenylate synthetase (OAS) activity in whole blood was assayed with Eiken's 2-5A RIA kit. Diluted blood was mixed with polyI:C-agarose gel, ATP was added after washing the gel, and the 2-5A produced was assayed by the RIA method (Shindo, M. et al., Hepatology, 9:715–719 (1989)). The assays were performed twice in each sample. For the estimation of the level of blood OAS, at least three mice were used.

Example 4

Reduced ALT, Reduced HCV Viral Titer, and Induction of OAS by Oral Administration of IFN-τ in Human Patients A. IFN-τ Preparation On day one, one bottle of IFNτ (SEQ ID NO:3) was removed from the refrigerator and the patient self-administered the proper volume of test material according to Table 2. IFNτ (SEQ ID NO:2) may also be prepared and administered in the same manner.

TABLE 2

Recombinant Ov-IFN-τ Patient Dose Administration

| Dose Group | Number of Patients | Ov-IFN-τ (mg/mL) | Volume (mL) per Dose (TID) | Total Daily Dose (mg) |
|---|---|---|---|---|
| I | 6 | 1.0 | 0.33 | 1.0 |
| II | 6 | 1.0 | 1.0 | 3.0 |
| III | 6 | 1.0 | 3.0 | 9.0 |
| IV | 6 | 1.0 | 5.0 | 15.0 |

B. Patient Dosing Instructions

All vials of test material and syringes were kept in a refrigerator maintained at 2 to 8° C. Prior to the self-administration of medication, the patient removed one vial and one syringe from the refrigerator. The cap was removed from the tip of the syringe and the tip of the syringe was placed into the bottle of medication to withdraw the appropriate volume into the syringe as instructed at the clinic on Day 1.

The tip of the syringe was placed in the mouth and the syringe contents were emptied into the mouth by depressing the plunger. The patient then swallowed the test material. If desired, the patient was allowed to drink a glass of water. The patient noted on his/her diary card the date and time the dose of test material was administered.

The above steps were repeated three times per day at approximately eight-hour intervals: once in the morning, once at midday, and once in the evening.

C. Results

Blood samples were taken at defined intervals over a 169 day test period. The samples were analyzed for 2',5'-oligoadenylate synthetase (OAS) levels in the serum and in the peripheral blood mononuclear cells (PBMC) using a 2-5A RIA kit (Eiken Chemical, Tokyo). Diluted blood was mixed with polyI:C-agarose gel, ATP was added after washing the gel, and the 2-5A produced was assayed by the RIA method (Shindo, M. et al., Hepatology, 9:715–719 (1989)). The assays, performed twice in each sample. The viral titer of hepatitis C, using reverse-transcriptase polymerase chain reaction, and the serum concentration of alanine aminotransferase (ALT) were also determined.

The results for each subject are shown in Tables 3–5 below, and graphically in FIGS. 7–8. An increase in OAS levels, and a decrease in both ALT and viral titer levels following oral ovine IFN-τ administration was observed.

TABLE 3A

Viral Titer, ALT and 2-5A Levels in Three Patients in Dose Group 1 (0.33 mg IFNτ three times daily)

| Patient Initials/# | Timepoint | HCV RT-PCR | ALT (IU/L) | Serum OAS pmol/dL |
|---|---|---|---|---|
| PAB/001 | Screen | 790,000 | 64 | 12.46 |
| PAB/001 | Day 1 | 290,000 | 63 | 10.00 |
| PAB/001 | Day 2 | — | — | 10.00 |
| PAB/001 | Day 3 | 1,700,000 | 57 | 5.00 |
| PAB/001 | Day 8 | 530,000 | 56 | 5.00 |
| PAB/001 | Day 15 | 580,000 | 61 | — |
| PAB/001 | Day 22 | 13,000 | 66 | 2.50 |
| PAB/001 | Day 29 | 230,000 | 40 | 10.00 |
| PAB/001 | Day 43 | — | 42 | 7.50 |
| PAB/001 | Day 57 | 640,000 | 37 | 16.67 |
| PAB/001 | Day 71 | — | — | 12.46 |
| PAB/001 | Day 85 | 960,000 | 50 | 13.86 |
| PAB/001 | Day 113 | 160,000 | 53 | 0.00 |
| MSM/002 | Screen | 4,600,000 | 258 | 11.05 |

TABLE 3A-continued

Viral Titer, ALT and 2-5A Levels in Three Patients in Dose Group 1 (0.33 mg IFNτ three times daily)

| Patient Initials/# | Timepoint | HCV RT-PCR | ALT (IU/L) | Serum OAS pmol/dL |
|---|---|---|---|---|
| MSM/002 | Day 1 | 5,100,000 | 164 | 16.67 |
| MSM/002 | Day 2/24 hr. | — | — | 10.00 |
| MSM/002 | Day 3 | 6,300,000 | 154 | 29.30 |
| MSM/002 | Day 8 | 5,100,000 | 133 | 33.08 |
| MSM/002 | Day 15 | 9,100,000 | 100 | 54.62 |
| MSM/002 | Day 22 | — | 103 | 51.54 |
| MSM/002 | Day 29 | 8,600,000 | 91 | 28.60 |
| MSM/002 | Day 43 | — | 86 | 12.46 |
| MSM/002 | Day 57 | 3,400,000 | 82 | 18.77 |
| MSM/002 | Day 71 | — | — | 36.15 |
| MSM/002 | Day 85 | 3,700,000 | 49 | 26.14 |
| MSM/002 | Day 113 | 3,800,000 | 64 | 42.31 |
| DMA/003 | Screen | 780,000 | 115 | 28.60 |
| DMA/003 | Day 1 | 990,000 | 115 | 26.14 |
| DMA/003 | Day 3 | 660,000 | 121 | 30.00 |
| DMA/003 | Day 8 | 920,000 | 105 | 36.15 |
| DMA/003 | Day 15 | 580,000 | 107 | 26.14 |
| DMA/003 | Day 22 | — | 105 | 24.74 |
| DMA/003 | Day 29 | 170,000 | 97 | 27.54 |
| DMA/003 | Day 43 | — | 85 | 23.33 |
| DMA/003 | Day 57 | 650,000 | 74 | 59.23 |
| DMA/003 | Day 71 | — | — | 36.15 |
| DMA/003 | Day 85 | 11,000 | 49 | 16.00 |
| DMA/003 | Day 107 | 880,000 | 45 | — |
| DMA/003 | Day 115 | 50,000 | 55 | 20.24 |
| DMA/003 | — | 460,000 | 47 | — |

TABLE 3B

Viral Titer, ALT and 2-5A Levels in Three Patients in Dose Group 1 (0.33 mg IFNτ three times daily)

| Patient Initials/# | Timepoint | HCV RT-PCR | ALT (IU/L) | Serum OAS pmol/dL |
|---|---|---|---|---|
| LER/004 | Screen | 6,100,000 | 118 | 33.95 |
| LER/004 | Day 1 | 6,000,000 | 108 | 33.95 |
| LER/004 | Day 3 | 11,000,000 | 120 | 53.68 |
| LER/004 | Day 8 | 1,900,000 | 109 | 29.51 |
| LER/004 | Day 15 | 3,400,000 | 120 | 41.84 |
| LER/004 | Day 22 | — | 94 | 34.74 |
| LER/004 | Day 29 | 640,000 | 109 | 43.42 |
| LER/004 | Day 43 | — | 99 | 49.74 |
| LER/004 | Day 57 | 4,400,000 | 106 | 37.89 |
| LER/004 | Day 71 | — | — | 81.00 |
| LER/004 | Day 85 | 3,900,000 | 67 | 3.20 |
| LER/004 | Day 113 | 3,200,000 | 107 | — |
| Z-I/005 | Screen | 3,400,000 | 151 | 43.42 |
| Z-I/005 | Day 1 | 4,600,000 | 134 | 43.42 |
| Z-I/005 | Day 2 | — | 144 | 45.00 |
| Z-I/005 | Day 3 | 1,400,000 | 109 | 46.58 |
| Z-I/005 | Day 8 | 4,000,000 | 94 | 12.93 |
| Z-I/005 | Day 15 | 1,100,000 | 107 | 48.95 |
| Z-I/005 | Day 22 | — | 107 | 47.37 |
| Z-I/005 | Day 29 | 2,200,000 | 144 | 74.82 |
| Z-I/005 | Day 43 | — | 111 | 26.10 |
| Z-I/005 | Day 57 | 4,400,000 | 122 | 43.42 |
| Z-I/005 | Day 71 | — | — | 10.00 |
| Z-I/005 | Day 85 | 1,100,000 | 122 | 17.80 |
| Z-I/005 | Day 113 | 3,200,000 | 132 | — |
| JRJ/006 | Screen | 21,000,000 | 111 | 52.11 |
| JRJ/006 | Day 1 | 8,500,000 | 104 | 21.90 |
| JRJ/006 | Day 3 | 6,000,000 | 98 | 26.53 |
| JRJ/006 | Day 8 | 950,000 | 124 | 24.21 |
| JRJ/006 | Day 15 | 3,700,000 | 118 | 19.09 |
| JRJ/006 | Day 22 | — | 109 | 22.07 |
| JRJ/006 | Day 29 | 3,300,000 | 93 | 19.75 |
| JRJ/006 | Day 43 | — | 122 | 24.88 |
| JRJ/006 | Day 57 | 7,000,000 | 78 | 35.62 |
| JRJ/006 | Day 71 | — | — | 52.92 |

TABLE 3B-continued

Viral Titer, ALT and 2-5A Levels in Three Patients in Dose Group 1 (0.33 mg IFNτ three times daily)

| Patient Initials/# | Timepoint | HCV RT-PCR | ALT (IU/L) | Serum OAS pmol/dL |
|---|---|---|---|---|
| JRJ/006 | Day 85 | 5,000,000 | 88 | 42.92 |
| JRJ/006 | Day 113 | >5,000,000 | — | — |

TABLE 4

Viral Titer, ALT and 2-5A Levels in Three Patients in Dos Group 2 (1 mg IFNτ three times daily)

| Patient Initials/# | Timepoint | HCV RT-PCR | ALT (IU/L) | Serum OAS pmol/dL |
|---|---|---|---|---|
| AMC/007 | Screen | 1,700,000 | 44 | 11.20 |
| AMC/007 | Day 1 | 1,300,000 | 48 | 18.40 |
| AMC/007 | Day 3 | 810,000 | 44 | 27.60 |
| AMC/007 | Day 8 | 630,000 | 50 | 42.40 |
| AMC/007 | Day 15 | 290,000 | 54 | 50.67 |
| AMC/007 | Day 22 | — | 53 | 94.50 |
| AMC/007 | Day 29 | 410,000 | 36 | 120.00 |
| AMC/007 | Day 43 | — | 29 | 81.33 |
| AMC/007 | Day 57 | 930,000 | 36 | 55.33 |
| AMC/007 | Day 71 | — | — | 51.33 |
| AMC/007 | Day 85 | — | — | — |
| AMC/007 | Day 113 | — | — | — |
| AMC/007 | Day 169 | — | — | — |
| ALW/008 | Screen | 30,000,000 | 47 | 53.33 |
| ALW/008 | Day 1 | 3,000,000 | 38 | 10.00 |
| ALW/008 | Day 3 | 3,200,000 | 42 | 42.00 |
| ALW/008 | Day 8 | 5,400,000 | 31 | 14.40 |
| ALW/008 | Day 15 | 17,000,000 | 29 | 10.00 |
| ALW/008 | Day 22 | — | 27 | 10.40 |
| ALW/008 | Day 29 | 11,000,000 | 25 | 10.00 |
| ALW/008 | Day 43 | — | 40 | 14.40 |
| ALW/008 | Day 57 | 18,000,000 | 31 | 12.80 |
| ALW/008 | Day 71 | — | — | 16.40 |
| ALW/008 | Day 85 | — | — | — |
| ALW/008 | Day 113 | — | — | — |
| ALW/008 | Day 169 | — | — | — |
| DBF/012 | Screen | 5,300,000 | 84 | 28.80 |
| DBF/012 | Day 1 | 9,300,000 | 77 | 26.00 |
| DBF/012 | Day 3 | 9,400,000 | 71 | 10.00 |
| DBF/012 | Day 8 | 7,900,000 | 86 | 53.33 |
| DBF/012 | Day 15 | 9,100,000 | 67 | 108.00 |
| DBF/012 | Day 22 | — | 64 | 42.67 |
| DBF/012 | Day 29 | 9,900,000 | 58 | 52.00 |
| DBF/012 | Day 43 | — | 61 | 58.00 |
| DBF/012 | Day 57 | 15,000,000 | 70 | 61.33 |
| DBF/012 | Day 71 | — | — | 168.00 |
| DBF/012 | Day 85 | — | — | — |
| DBF/012 | Day 113 | — | — | — |
| DBF/012 | Day 169 | — | — | — |

TABLE 5

Viral Titer, ALT and 2-5A Levels in Three Patients in Dose Group 3 (3 mg IFNτ three times daily)

| Patient Initials/# | Timepoint | HCV RT-PCR | ALT (IU/L) | Serum OAS pmol/dL | PBMC OAS pmol/5 × 10$^6$ PBMC/mL |
|---|---|---|---|---|---|
| VCC/009 | Screen | 5,100,000 | 113 | 17.20 | — |
| VCC/009 | Day 1 | 4,300,000 | 128 | 58.67 | 286.88 |
| VCC/009 | Day 2 | — | — | 10.00 | — |
| VCC/009 | Day 3 | 3,500,000 | 126 | 18.40 | 218.57 |
| VCC/009 | Day 8 | 1,600,000 | 130 | 24.80 | — |
| VCC/009 | Day 15 | 2,200,000 | 118 | 25.20 | 624.38 |
| VCC/009 | Day 22 | — | 99 | 18.00 | — |
| VCC/009 | Day 29 | 1,500,000 | 93 | 30.67 | 1261.43 |
| VCC/009 | Day 43 | — | 72 | 15.20 | — |
| VCC/009 | Day 57 | 2,700,000 | 62 | 10.00 | — |
| VCC/009 | Day 71 | — | — | 18.40 | — |
| VCC/009 | Day 85 | — | — | — | — |
| VCC/009 | Day 113 | — | — | — | — |
| VCC/009 | Day 169 | — | — | — | — |
| HCM/010 | Screen | 3,00,000 | 60 | 28.84 | — |
| HCM/010 | Day 1 | 5,000,000 | 47 | 12.31 | 998.1 |
| HCM/010 | Day 2/24 hr. | — | — | — | — |
| HCM/010 | Day 3 | 5,100,000 | 52 | 22.56 | 1336.67 |
| HCM/010 | Day 8 | 5,100,000 | 50 | 18.6 | — |
| HCM/010 | Day 15 | 5,300,000 | 49 | 30 | 1336.67 |
| HCM/010 | Day 22 | — | 49 | 47.08 | — |
| HCM/010 | Day 29 | 3,000,000 | 57 | 50 | 1524.76 |
| HCM/010 | Day 43 | — | 45 | 246 | — |
| HCM/010 | Day 57 | 4,300,000 | 59 | 16.67 | — |
| HCM/010 | Day 71 | — | — | 15.26 | — |
| HCM/010 | Day 85 | — | — | — | — |
| HCM/010 | Day 113 | — | — | — | — |
| HCM/010 | Day 169 | — | — | — | — |
| CLR/011 | Screen | 12,000,000 | 58 | 10.00 | — |
| CLR/011 | Day 1 | 19,000,000 | 66 | 30.00 | 960.48 |
| CLR/011 | Day 3 | 28,000,000 | 55 | 11.05 | 922.86 |
| CLR/011 | Day 8 | >5,000,000 | 55 | 12.46 | — |
| CLR/011 | Day 15 | 23,000,000 | 63 | 12.46 | 1035.71 |
| CLR/011 | Day 22 | — | 65 | 19.82 | — |
| CLR/011 | Day 29 | 13,000,000 | 58 | 10.00 | 998.1 |
| CLR/011 | Day 43 | — | 63 | 36.00 | — |
| CLR/011 | Day 57 | 18,000,000 | 61 | 20.80 | — |
| CLR/011 | Day 71 | — | — | 10.00 | — |
| CLR/011 | Day 85 | — | — | — | — |
| CLR/011 | Day 113 | — | — | — | — |
| CLR/011 | Day 169 | — | — | — | — |

Example 5

Orally-Administered OvIFNτ Blocks Development of Experimental Allergic Encephalomyelitis Recipient New Zealand White (NZW) mice received OvIFτ ($10^5$ U/ml) by either i.p. injection or oral feeding 48 hours prior to, on the day of, and 48 hours after immunization with bovine myelin basic protein (bMBP) for induction of experimental allergic encephalomyelitis (EAE). $10^5$ U of IFNτ were mixed with PBS to a total volume of 100 μL and administered using a feeding tube placed down the esophagus and into the stomach. The dilution of the IFNτ in phosphate buffered saline was done immediately before administration.

For induction of EAE in NZW mice, 300 μg of bovine myelin basic protein (bMBP) was emulsified in complete Freund's adjuvant (CFA) containing 8 mg/mL of H37Ra (Mycobacterium tuberculosis, Difco, Detroit, Mich.) and injected on either side of the base of the tail. On the day of immunization and 48 hours later, 400 ng of Pertussis toxin (List Biologicals, Campbell, Calif.) was also injected. For induction of EAE in SJL/J mice, the same protocol was used as described except mice were immunized again 7 days after the initial immunization. Mice were examined daily for signs of EAE and severity of disease was graded on the following scale:

| SCORE | SYMPTOM/SEVERITY |
|---|---|
| 1 | loss of tail tone |
| 2 | hind limb weakness |
| 3 | paraparesis |
| 4 | paraplegia |
| 5 | moribund/death |

To determine whether prevention of EAE was specific to OvIFNτ treatment, an anti-OvIFNτ monoclonal antibody (mAb), HL127, was used to neutralize OvIFNτ ability to block EAE (antibody HL127, directed against amino acid residues 139–172 of SEQ ID NO:2, neutralizes the antiviral activity of OvIFNτ in an antiviral assay using the MDBK cell line). A 1:10 dilution of HL127 was incubated for 2 hours with OvIFNτ prior to administration by either i.p. injection or oral feeding. Antibodies directed against IFNτ antigens, may be generated using the information herein combined with known techniques for antibody production (e.g., Harlow, E., et al. in ANTIBODIES: A LABORATORY MANUAL, Cold Spring Harbor Laboratory Press, Cold Spring Harbor, N.Y. (1988)).

The results are shown in Table 6, below. Both oral feeding and i.p. injection of OvIFNτ protected against acute induction of EAE. None of the animals that received IFNτ via i.p. injection developed symptoms of EAE, while of the animals that received IFNτ orally, 7 of 9 (78%) were protected. Anti-OvIFNτ antibody HL127 was effective at partially neutralizing the ability of the OvIFNτ to block EAE. These data indicate that orally-administered IFNτ is effective as a treatment in an animal model of multiple sclerosis.

TABLE 6

Effect of Orally Administered IFNτ on Onset and Severity of Acute EAE in Mice

| ROUTE OF ADMINISTRATION | TREATMENT | DISEASE INCIDENCE | MEAN DAY OF ONSET | MEAN SEVERITY |
|---|---|---|---|---|
| i.p. | saline | 4/4 | 24.8 ± 2.1 | 2.5 ± 0 |
| i.p. | OvIFNτ | 0/4 | — | — |
| i.p. | OvIFNτ + HL127Ab | 3/4 | 20.7 ± 1.2 | 2.3 ± 0.6 |
| oral | saline | 7/9 | 22.0 ± 1.0 | 2.7 ± 0.6 |
| oral | OvIFNτ | 2/9 | 19 | 3 |
| oral | OvIFNτ + HL127Ab | 5/8 | 20.7 ± 0.6 | 3 ± 0 |

OvIFNτ ($10^5$ U) was administered 48 hours prior to MBP immunization, on the day of MBP immunization and 48 hours after MBP immunization by either i.p. injection or oral feeding. HL127, a monoclonal antibody specific for OvIFNτ, was incubated with OvIFNτ for two hours prior to administration.

Example 6

Detection of OvIFNτ in Sera Following Oral Administration

The amount of OvIFNτ detectable in the sera of mice (treated as above) was compared over time after oral feeding or i.p. injection of OvIFNτ. Mice were administered $3 \times 10^5$ U of OvIFNτ and bled at 0.5, 2, 4, 6, 24 and 48 hours following IFNτ administration. Sera were tested in a cytopathic effect (viral plaque) assay (Familetti, P. C. et al., Meth. Enzymol. 78:387 (1981)) to determine the amount of IFNτ in the samples.

Briefly, dilutions of IFNτ were added to MDBK cells grown to confluency in a flat bottom 96 well plate and incubated for 18 to 24 hours at 37° C. Vesicular stomatatosis virus (VSV) was added to the plate for 45 minutes at room temperature. Virus was removed and methyl cellulose was added and the plate incubated for 48 hours at 37° C. After removal of methyl cellulose, the plate was stained with crystal violet for visualization of plaques. For measurement of IFN neutralization, OvIFNτ at a concentration of 500 U/mL was incubated for 1 hour at 37° C. with either sera or HL127 (a monoclonal antibody specific for OvIFNτ). One antiviral unit caused a 50% reduction in destruction of the monolayer, relative to untreated MDBK cells infected with VSV (control plates). All samples were assayed simultaneously to eliminate interassay variability.

As shown in FIG. 9, OvIFNτ was detected at 0.5 hour and 2 hours after oral feeding (filled bars) at levels of 200 U/mL. By comparison, somewhat higher levels of OvIFNτ were detected for over a 24 hour period of time after i.p. injection (open bars). These data show that the above dose of IFNτ can be detected in serum for about two hours following oral administration.

Example 7

Prevention of Chronic Relapse of Experimental Allergic Encephalomyelitis by Orally-Administered OvIFNτ

The ability of OvIFNτ to prevent paralysis was examined using a chronic-relapsing model of EAE, in which SJL mice immunized with MBP develop a chronic form of the disease where the appearance of symptoms occurs in a relapsing-remitting manner (Zamvil, S. S. et al., Ann. Rev. Immunol. 8:579–621 (1990)).

EAE was induced in SJL mice essentially as described above. The mice were treated with $10^5$ U of IFNτ by either i.p. injection or oral feeding on the day of immunization (day 0) and every 48 hours thereafter for the duration of the experiment. The results are presented in FIG. 10A, SJL mice which were immunized with MBP but did not receive IFNτ treatment developed chronic relapsing paralysis with a 5/5 incidence of disease, with a peak mean severity of ~2.5 occurring 14 days after the start of the experiment. In contrast, treatment with OvIFNτ by either i.p. injection or oral feeding (FIGS. 10B and 10C, respectively) resulted in protection from EAE. Incidence of disease in both IFNτ treatment groups was reduced to ⅕ animals, with a mean severity of ~1.0. These data indicate that oral administration of IFNτ can block the development of chronic relapsing EAE, and suggest that orally-administered IFNτ may be as effective as i.p. injection when the IFNτ is fed about every 48 hours over an extended period of time.

Example 8

Histological Analysis

Histological analyses were performed to determine the extent of lymphocyte infiltration into the CNS of MBP-immunized mice treated with OvIFNτ by oral and i.p. routes.

Mice were perfused with 4% paraformaldehyde, vertebral columns were removed and treated with formalin for 2 to 3 days. Spinal cords were dissected out and soaked in 0.5% sucrose overnight at 4° C. Spinal cord sections were embedded and sections cut in a microtome. Sections were fixed to slides in 4% paraformaldehyde and stained with cresyl violet for visualization of inflammatory infiltrates.

The results are shown in FIGS. 11A–11C at a final magnification of 222×. Lymphocytic lesions were present in control spinal cord white matter (FIG. 11A). In contrast, no lymphocytic infiltrates were detected in mice treated with OvIFNτ by i.p. injection (FIG. 11B) or oral feeding (FIG. 11C). These data suggest that the protective effect of IFNτ is associated with inhibition of lymphocyte infiltration of the CNS.

Example 9

Induction of IL-10 by Treatment with OvIFNτ

During the course of OvIFNτ treatment of SJL for prevention of chronic relapsing EAE, mice were bled and sera were examined for the presence of interleukin 10 (IL-10). Sera from mice which received either a single IFNτ ($10^5$ U) treatment (by i.p. injection or oral feeding), prolonged IFNτ ($10^5$ U) treatment (by i.p. injection or oral treatment for greater than 20 days) or no treatment were examined for IL-10 by enzyme-linked immunosorbent assay (ELISA) using IL-10 ELISA kits (Genzyme, Cambridge, Mass.) following the manufacturer's instructions. All sera samples were tested in duplicate.

For use in treating a cell-proliferation condition, IFNτ is administered at a dose sufficient to achieve an initial measurable increase in blood OAS in the patient. Thereafter, treatment is continued at an effective dose, independent of further changes in blood OAS levels, for example, a fall in OAS blood levels due to a reduction in cancer cells in the body. Administration of IFNτ at an effective dose is continued until a desired level of regression is observed, as measured for example, by tumor size or extent of cancer cells in particular tissues. The patient may be co-treated during the treatment period with a second anticancer agent, e.g., cis-platin, doxorubicin, or taxol al feeding), prolonged IFNτ ($10^5$ U) treatment (by i.p. injection or oral treatment for greater than 20 days) or no treatment were examined for IL-10 by enzyme-linked immunosorbent assay (ELISA) using IL-10 ELISA kits (Genzyme, Cambridge, Mass.) following the manufacturer's instructions. All sera samples were tested in duplicate.

Figure 12:
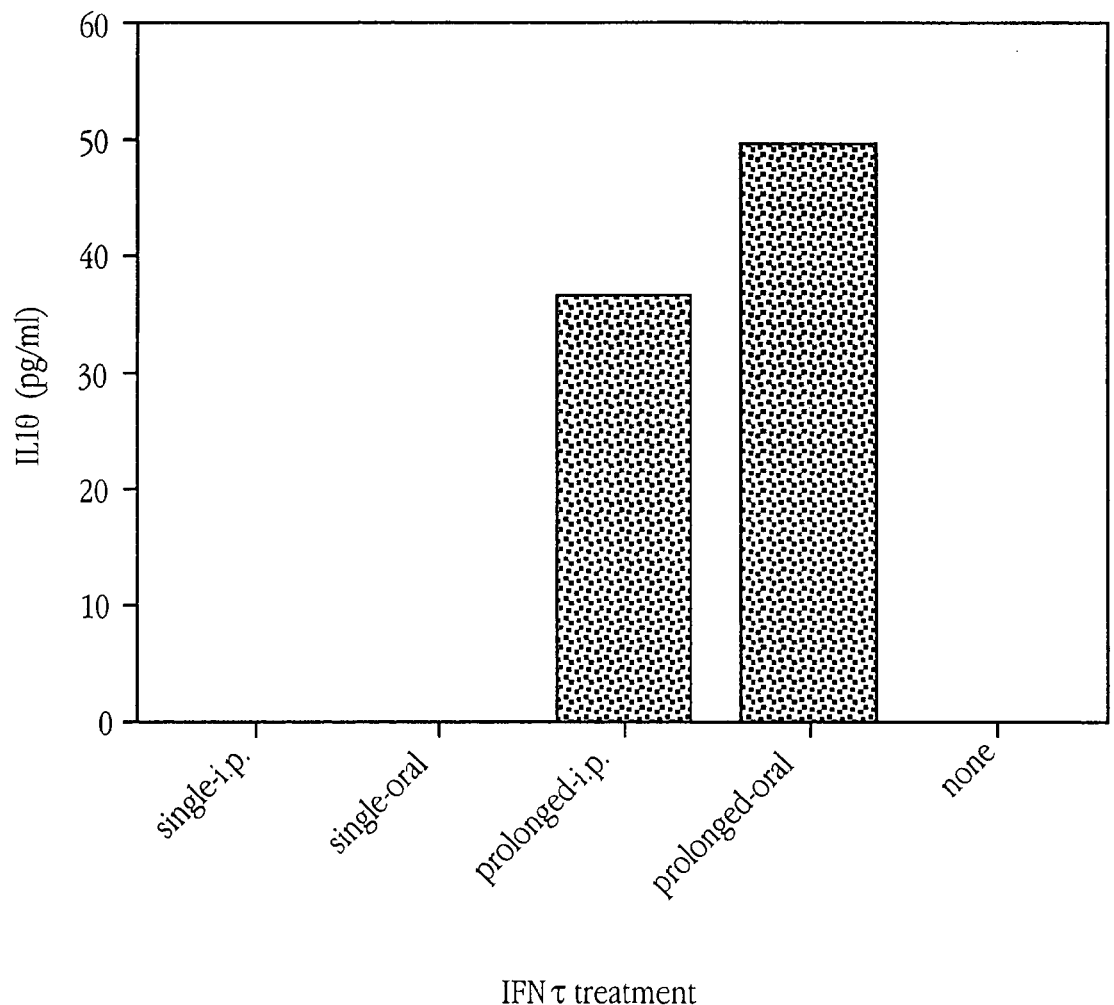
FIG. 12 shows induction of IL-10 by either single-dose or prolonged IFNτ treatment administered by i.p. injection or oral feeding.

The results are shown in FIG. 12. No IL-10 was detected in control mice or in mice which received a single treatment of OvIFNτ by either i.p. injection or oral feeding. In contrast, SJL mice which received OvIFNτ by either i.p. injection or oral feeding every 48 hours for greater than 20 days had detectable levels of IL-10 in their sera. These data suggest that IFNτ-induced production of IL-10 may be a contributing mechanism by which OvIFNτ prevents development of EAE.

Example 10

Cessation of Treatment with OvIFNτ Results in Relapsing Paralysis

SJL mice which were protected from EAE by OvIFNτ treatment via i.p. injection or oral feeding (every 48 hours) were followed for 58 days, during which time no disease development was observed. Treatment with OvIFNτ was then removed and the mice were observed for an additional 22 days for symptoms of disease.

The results are shown in FIG. 13. IFNτ treatment is denoted as plus signs and removal of IFNτ treatment is denoted as minus signs beneath the graph. Disease incidence in each treatment group was as follows: PBS control=3/4 (square); i.p. injection=3/3 (triangle); oral feeding=3/4 (circle).

Both groups of mice which had previously been protected from EAE by OvIFNτ treatment developed signs of paralysis 6 to 12 days after removal of the OvIFNτ treatment. These data indicate that ongoing administration of IFNτ, by either i.p. injection or oral feeding, is desirable for continued protection from EAE in the chronic-relapsing model of EAE.

Example 11

Oral Administration of OvIFNτ Reduces Anti-OvIFNτ Antibody Response

After removal of OvIFNτ treatment in the experiments described in Example 10, above, mice from each treatment group were bled and sera were examined for the presence of anti-OvIFNτ antibodies (Ab).

The antigen, OvIFNτ, was adsorbed to the flat bottoms of plastic tissue culture wells overnight at a concentration of 600 ng/well, and subsequently evaporated to dryness. The plates were treated with 5% milk (Carnation) in PBS for 2 hours in order to block nonspecific binding and then washed 3 times with PBS containing 0.05% Tween 20. Various dilutions of sera from mice which were untreated, OvIFNτ treated by i.p. injection, and OvIFNτ treated by oral feeding were added and incubated for 3 hours. Binding was assessed with goat anti-mouse immunoglobulin coupled to horseradish peroxidase. Color development was monitored at 492 nm in an ELISA plate reader (Bio-Rad, Richmond, Calif.) after o-phenylenediamine and $H_2O_2$ were added and the reaction terminated with 2M $H_2SO_4$.

Figure 14:
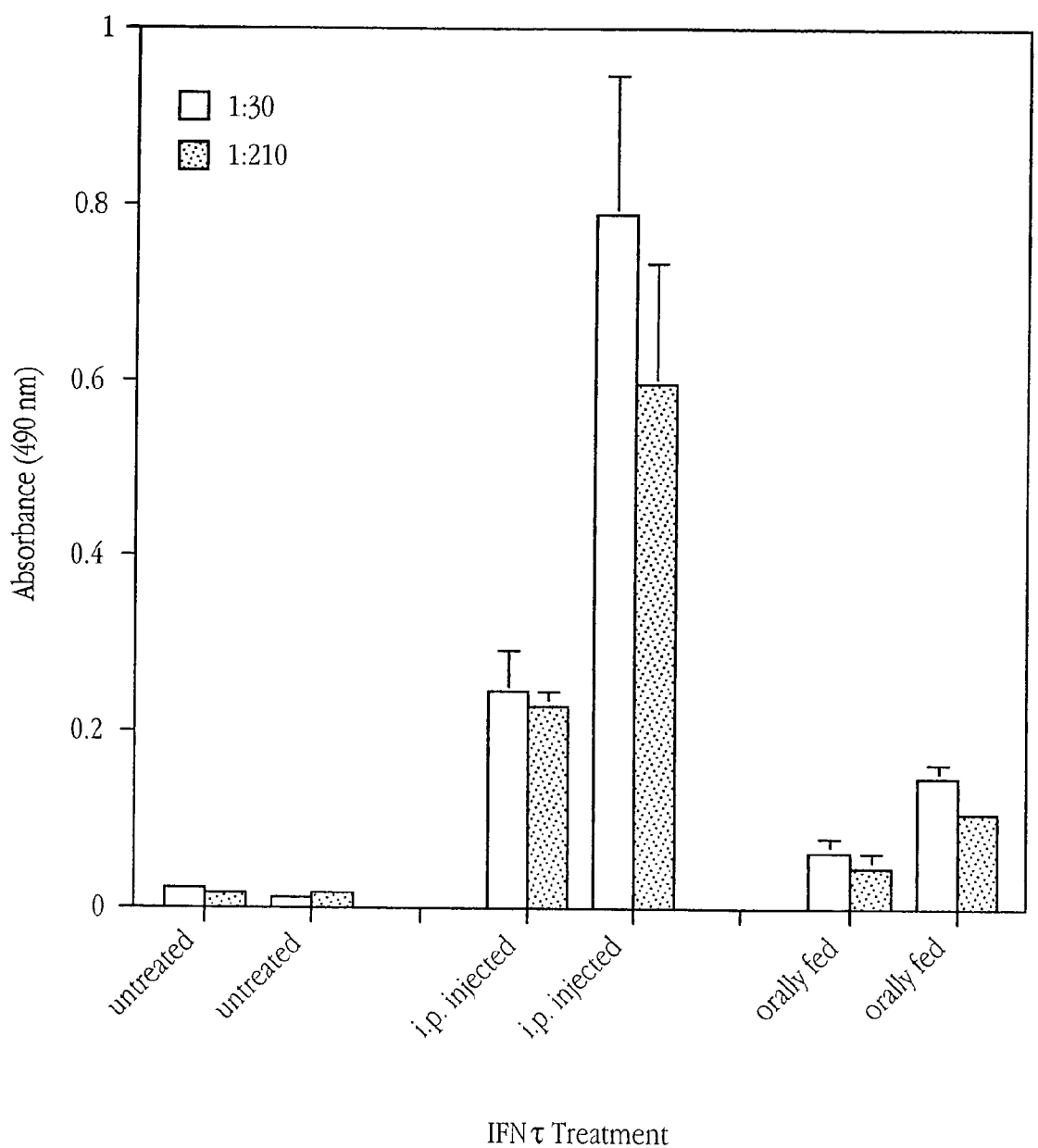
FIG. 14 shows ELISA detection of anti-IFNτ antibodies in the sera of IFNτ-treated mice following i.p. injection or oral feeding of IFNτ.

Exemplary results are shown in FIG. 14. Sera from untreated, OvIFNτ treated-i.p. injected and OvIFNτ treated-orally fed (2 mice/group) were examined by ELISA using multiple dilutions, including 1:30 (open bars) and 1:120 (filled bars). Mice which received OvIFNτ by oral feeding exhibited minimal antibody levels while mice which received OvIFNτ by i.p. injection exhibited elevated levels of anti-OvIFNτ Ab. As expected, mice which received no OvIFNτ treatment displayed no anti-OvIFNτ Ab.

Sera were also examined for their ability to neutralize OvIFNτ antiviral activity on MDBK cells as described above. The results are shown in Table 7, below. None of the sera from either i.p. injected or orally fed mice possessed neutralizing activity. These data suggest that oral treatment with IFNτ circumvents the antibody response directed against OvIFNτ protein observed in i.p. injection-treated individuals, and that neither treatment typically results in the generation of neutralizing antibodies.

TABLE 7

| Sera OvIFNτ Titer in Mice Treated with OvIFNτ | |
|---|---|
| 500 U/ML OF OvIFNτ CO-CULTURED WITH SERA FROM: | OvIFNτ TITER (U/ML) |
| untreated | 500 |
| i.p. injected | 500 |
| orally fed | 500 |
| HL127 | <50 |

Although the invention has been described with respect to particular embodiments, it will be apparent to those skilled in the art that various changes and modifications can be made without departing from the invention.

What is claimed is:

1. A method for treating a condition responsive to interferon tau therapy, wherein the condition is selected from an autoimmune condition, cancer, or a viral infection, in a human subject, comprising orally administering interferon-tau to the intestinal tract of the subject in an amount effective to produce a measurable increase in the subject's blood 2', 5'-oligoadenylate synthetase (OAS) level, relative to the blood OAS level in the subject in the absence of interferon-tau administration, as evidenced by monitoring the subject's blood OAS level to ascertain if the OAS level is increased following said administering, wherein said amount of interferon-tau is at least about $4.9 \times 10^8$ Units/day, and continuing to administer interferon-tau to the intestinal tract of the subject in such effective amount, on a regular basis of at least several times per week, for a period of at least one month, independent of changes in the subject's blood OAS level.

2. The method of claim 1, wherein said interferon-tau is an *ovine* interferon-tau having a sequence identified as SEQ ID NO:2 or SEQ ID NO:3.

3. The method of claim 1, wherein said continuing administration is carried out on a daily basis.

4. The method of claim 1, for treatment of multiple sclerosis in the subject, wherein said continuing administration is carried out during the period of patient symptoms.

5. The method of claim 1, for treatment of hepatitis C infection in the subject, which further includes detecting the presence of infection in the subject, and said continuing administration is carried out for a period of several months past the time when no viral infection is detected in the subject.

6. The method of claim 1, for treatment of cancer in the subject, which further includes administered an anticancer agent to the subject during the period of continuing administration of interferon-tau.

* * * * *

SEQUENCE LISTING

<160> NUMBER OF SEQ ID NOS: 4

<210> SEQ ID NO 1
<211> LENGTH: 516
<212> TYPE: DNA
<213> ORGANISM: Ovis aries

<400> SEQUENCE: 1

```
tgctacctgt cgcgaaaact gatgctggac gctcgagaaa atttaaaact gctggaccgt    60
atgaatcgat tgtctccgca cagctgcctg caagaccgga agacttcgg tctgccgcag    120
gaaatggttg aaggtgacca actgcaaaaa gaccaagctt tcccggtact gtatgaaatg    180
ctgcagcagt ctttcaacct gttctacact gaacattctt cggccgcttg ggacactact    240
cttctagaac aactgtgcac tggtctgcaa cagcaactgg accatctgga cacttgccgt    300
ggccaggtta tgggtgaaga agactctgaa ctgggtaaca tggatccgat cgttactgtt    360
aaaaaatatt tccagggtat ctacgactac ctgcaggaaa aggttactc tgactgcgct    420
tgggaaatcg tacgcgttga atgatgcgg gccctgactg tgtcgactac tctgcaaaaa    480
cggttaacta aatgggtgg tgacctgaat tctccg                                516
```

<210> SEQ ID NO 2
<211> LENGTH: 172
<212> TYPE: PRT
<213> ORGANISM: Ovis aries

<400> SEQUENCE: 2

```
Cys Tyr Leu Ser Arg Lys Leu Met Leu Asp Ala Arg Glu Asn Leu Lys
 1               5                  10                  15

Leu Leu Asp Arg Met Asn Arg Leu Ser Pro His Ser Cys Leu Gln Asp
             20                  25                  30

Arg Lys Asp Phe Gly Leu Pro Gln Glu Met Val Glu Gly Asp Gln Leu
         35                  40                  45

Gln Lys Asp Gln Ala Phe Pro Val Leu Tyr Glu Met Leu Gln Gln Ser
     50                  55                  60

Phe Asn Leu Phe Tyr Thr Glu His Ser Ser Ala Ala Trp Asp Thr Thr
 65                  70                  75                  80

Leu Leu Glu Gln Leu Cys Thr Gly Leu Gln Gln Gln Leu Asp His Leu
                 85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

<210> SEQ ID NO 3
<211> LENGTH: 172
<212> TYPE: PRT
<213> ORGANISM: Artificial
<220> FEATURE:
<223> OTHER INFORMATION: recombinant IFNtau based on Ovis aries sequence

```
<400> SEQUENCE: 3

Cys Tyr Leu Ser Glu Arg Leu Met Leu Asp Ala Arg Glu Asn Leu Lys
1               5                   10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
                35                  40                  45

Gln Lys Asp Gln Ala Phe Pro Val Leu Tyr Glu Met Leu Gln Gln Ser
        50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
                100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

<210> SEQ ID NO 4
<211> LENGTH: 516
<212> TYPE: DNA
<213> ORGANISM: Artificial
<220> FEATURE:
<223> OTHER INFORMATION: recombinant IFNtau based on Ovis aries sequence

<400> SEQUENCE: 4
tgctacctgt cggagcgact gatgctggac gctcgagaaa atttaaaact gctggaccgt      60
atgaatcgat tgtctccgca cagctgcctg caagaccgga aagacttcgg tctgccgcag     120
gaaatggttg aaggtgacca actgcaaaaa gaccaagctt tcccggtact gtatgaaatg     180
ctgcagcagt ctttcaacct gttctacact gaacattctt cggccgcttg ggacactact     240
cttctagaac aactgtgcac tggtctgcaa cagcaactgg accatctgga cacttgccgt     300
ggccaagtta tgggtgaaga agactctgaa ctgggtaaca tggatccgat cgttactgtt     360
aaaaaatatt tccagggtat ctacgactac ctgcaggaaa aaggttactc tgactgcgct     420
tgggaaatcg tacgcgttga aatgatgcgg gccctgactg tgtcgactac tctgcaaaaa     480
cggttaacta aaatgggtgg tgacctgaat tctccg                               516
```